(12) United States Patent
Foody et al.

(10) Patent No.: US 10,087,476 B2
(45) Date of Patent: Oct. 2, 2018

(54) PROCESS FOR HYDROLYZING A PRETREATED FEEDSTOCK AND RECOVERING LIGNIN

(71) Applicant: Iogen Corporation, Ottawa (CA)

(72) Inventors: Brian E. Foody, Ottawa (CA); Kristin Martens, Nepean (CA); Patrick J. Foody, Ottawa (CA); Jeffrey S. Tolan, Ottawa (CA)

(73) Assignee: IOGEN CORPORATION, Ottawa (CA)

( * ) Notice: Subject to any disclaimer, the term of this patent is extended or adjusted under 35 U.S.C. 154(b) by 54 days.

(21) Appl. No.: 15/034,867

(22) PCT Filed: Dec. 4, 2014

(86) PCT No.: PCT/CA2014/051166
§ 371 (c)(1),
(2) Date: May 5, 2016

(87) PCT Pub. No.: WO2015/081439
PCT Pub. Date: Jun. 11, 2015

(65) Prior Publication Data
US 2016/0273011 A1 Sep. 22, 2016

Related U.S. Application Data

(60) Provisional application No. 61/912,710, filed on Dec. 6, 2013, provisional application No. 61/912,713, filed
(Continued)

(51) Int. Cl.
*C07G 1/00* (2011.01)
*C08H 8/00* (2010.01)
(Continued)

(52) U.S. Cl.
CPC ............... *C12P 19/14* (2013.01); *C07G 1/00* (2013.01); *C08H 6/00* (2013.01); *C08H 8/00* (2013.01);
(Continued)

(58) Field of Classification Search
CPC ...... C13K 1/02; C13K 13/002; C13K 13/007; C13K 13/00; C13K 11/00; C13K 1/00; C13K 1/04; C08H 8/00; C08H 6/00; C12P 2201/00; C12P 19/02; C12P 19/14; C12P 7/065; C12P 7/10; C12P 7/16; C12P 7/28; C12P 2203/00; C12P 5/023; C12P 7/00; C12P 7/08; C12P 7/18; C12P 7/40; C12P 7/54; C12P 7/012; C12P 7/04; C12P 3/00; C12P 19/00; C12P 7/14; C12P 7/46; B01D 3/002; B01D 3/143; B01D 3/145; B01D 3/148; B01D 3/001; C07G 1/00; C07H 19/00; C07H 3/02; C12M 21/04; C12M 45/06; C12M 45/09; C12M 41/12; C12M 47/10; C12M 21/18; C12M 43/02; C12M 45/02; D21C 11/0007; D21C 1/02; D21C 3/04; D21C 11/10; D21C 1/08; Y02E 50/16; Y02E 50/17; Y02E 50/10; Y02E 50/13; C08F 212/14; C08F 8/44; C08F 8/36; C08F 212/08; C08F 8/30; C08F 212/36; C08F 8/40; C08F 226/08; C08F 8/42; C08F 226/06; C08F 12/18; C08F 8/24; C08F 8/32; C08F 214/14; B01J 31/06; B01J 2231/005; B01J 2531/004; B01J 31/0271; B01J 35/026; C08G 8/28; Y02P 20/582; C08B 1/003; C12N 9/0006; C12N 9/0065; C12N 9/16; C12N 9/20;
(Continued)

(56) References Cited

U.S. PATENT DOCUMENTS 7,354,743 B2 4/2008 Vlasenko et al.
7,455,997 B2 11/2008 Hughes
(Continued)

FOREIGN PATENT DOCUMENTS

WO 2008/134037 A1 11/2008
WO 2009/105236 A1 8/2009
(Continued)

OTHER PUBLICATIONS

Borjesson et.al., "Effect of poly(ethylene glycol) on enzymatic hydrolysis and adsorption of cellulase enzymes to pretreated lignocellulose", Enzyme and Microbial Technology 41 (2007) 186-195.
Borjesson et.al. , "Enhanced enzymatic conversion of softwood lignocellulose by poly(ethylene glycol) addition", Enzyme and Microbial Technology 40 (2007) 754-762.
Caesar, "Separation of lignocellulosic material in wheat straw using steam explosion and ultrafiltration", Department of Chemical Engineering, Lund University, Sweden, Feb. 2011.
Chylenski et.al., "Precipitation of Trichoderma reesei commercial cellulase preparations under standard enzymatic hydrolysis conditions for lignocelluloses", Biotechnol Lett, 34 (2012) 1475-1482.
(Continued)

*Primary Examiner* — Deborah K Ware
(74) *Attorney, Agent, or Firm* — Knobbe Martens Olson & Bear, LLP

(57) ABSTRACT

A process for hydrolyzing a pretreated lignocellulosic feedstock is disclosed herein. The process comprises hydrolyzing the pretreated lignocellulosic feedstock with an enzyme mixture comprising at least cellulase enzymes to produce a hydrolyzed slurry comprising glucose and lignin solids. The hydrolyzing is conducted in the presence of a polymer, such as an aliphatic polyether. A solids-liquid separation is conducted to recover lignin solids from a process stream comprising the lignin solids and the polymer. A process stream is then obtained comprising recovered lignin solids resulting from the solids-liquid separation. Also provided are processes for recovering the polymer from the lignin solids and/or from solution.

20 Claims, 7 Drawing Sheets

Related U.S. Application Data on Dec. 6, 2013, provisional application No. 61/912,724, filed on Dec. 6, 2013.

(51) Int. Cl.
| | | |
|---|---|---|
| C12P 7/04 | (2006.01) | |
| C12P 7/10 | (2006.01) | |
| C12P 19/02 | (2006.01) | |
| C12P 19/14 | (2006.01) | |
| D21C 1/02 | (2006.01) | |
| D21C 3/04 | (2006.01) | |
| D21C 11/00 | (2006.01) | |
| C08H 7/00 | (2011.01) | |

(52) U.S. Cl.
CPC .................................. *C12P 7/04* (2013.01); *C12P 7/10* (2013.01); *C12P 19/02* (2013.01); *D21C 1/02* (2013.01); *D21C 3/04* (2013.01); *D21C 11/0007* (2013.01); *C12P 2201/00* (2013.01); *Y02E 50/16* (2013.01)

(58) Field of Classification Search
CPC .. C12N 9/2402; C12N 9/2437; C12N 9/2445; C12N 9/248; C12N 9/2485; C12Y 302/01; C12Y 302/01004; C12Y 302/01008; C12Y 302/01021; C12Y 302/01037; C12Y 302/01055; A23K 30/15; C07D 233/58; C07D 295/037; C07F 9/5407; C08L 97/005; C10L 1/026; C13B 10/14; C07K 14/195
See application file for complete search history.

(56) References Cited

U.S. PATENT DOCUMENTS

| 7,972,826 | B2 | 7/2011 | Larsen et al. | |
|---|---|---|---|---|
| 8,524,474 | B2 | 9/2013 | Sabesan et al. | |
| 8,987,509 | B2 * | 3/2015 | Tolan ....................... | B01D 3/02 562/512 |
| 2005/0164355 | A1 | 7/2005 | Vlasenko et al. | |
| 2011/0250645 | A1 | 10/2011 | Schiffino et al. | |
| 2012/0108798 | A1 | 5/2012 | Wenger et al. | |
| 2013/0244293 | A1 | 9/2013 | Balan et al. | |
| 2014/0309414 | A1 * | 10/2014 | Zhang ................. | C08B 37/0003 536/123.1 |

FOREIGN PATENT DOCUMENTS

| WO | 2011/007369 A1 | 1/2011 |
|---|---|---|
| WO | 2011/137150 A1 | 11/2011 |

OTHER PUBLICATIONS

Duarte et.al., "Polymer induced flocculation and separation of particulates from extracts of lignocellulosic materials", Bioresource Technology, 101 (2010) 8526-8534.
Eckard et.al., "Enzyme recycling in a simultaneous and separate saccharification and fermentation of corn stover: A comparison between the effect of polymeric micelles of surfactants and polypeptides", Bioresource Technology, 132 (2013) 202-209.
Eriksson et.al., "Mechanism of surfactant effect in enzymatic hydrolysis of lignocellulose", Enzyme and Microbial Technology, 31 (2002) 353-364.
Jonsson et.al., "Bioconversion of lignocellulose: inhibitors and detoxification", Biotechnoogy for Biofuels (2013) 6-16.
Kadla et.al., "Miscibility and Hydrogen Bonding in Blends of Poly(ethylene oxide) and Kraft Lignin", Macromolecules 36 (2003) 7803-7811.
Kouisni et.al., "Kraft Lignin Recovery and its Use in the Preparation of Lignin-Based Phenol Formaldehyde Resins for Plywood", Cellulose Chemistry and Technology, (2011) 45 (7-8), 515-520.
Kurakake et.al., "Pretreatment of Bagasse by Nonionic Surfactant for the Enzymatic Hydrolysis", Bioresource Technology, 49 (1994) 247-251.
Lindstrom et.al., "Selective Adsorption, Flocculation, and Fractionation of Wood Pulps with Polyethyleneoxide", Journal of Colloid and Interface Science, vol. 94. No. 2, Aug. 1983,404-411.
Liu et.al., "Separation of lignocellulosic materials by combined processes of pre-hydrolysis and ethanol extraction", Bioresource Technology, 102 (2011) 1264-1269.
Miller-Chou, "A review of polymer dissolution", Prog. Polym. Sci. 28 (2003) 1223-1270.
Montane et.al. "Fractionation of Wheat Straw by Steam-Explosion Pretreatment and Alkali Delignification. Cellulose Pulp and Byproducts from Hemicellulose and Lignin", Journal of Wood Chemistry and Technology, (1998) 18(2), 171-191.
Negro et.al., "Flocculation Mechanism Induced by Phenolic Resin/Peo and Floc Properties", AIChE Journal, Mar. 2005, vol. 51, No. 3, 1022-1031.
Norgren et.al., "Sulfate and Surfactants as Boosters of Kraft Lignin Precipitation", Ind. Eng. Chem. Res. (2009) 48, 5098-5104.
Ohman et.al., "Filtration Properties of Lignin Precipitated from Black Liquor", Tappi Journal, vol. 6, No. 7, Jul. 2007.
Ouyang et.al., "Enhanced saccharification of SO2 catalyzed steam-exploded corn stover by polyethylene glycol addition", Biomass and Bioenergy, 35 (2011) 2053-2058.
Oing et.al., "Impact of surfactants on pretreatment of corn stover", Bioresource Technology, 101 (2010) 5941-5951.
Shi et.al., "A combined acidification/PEO flocculation process to improve the lignin removal from the pre-hydrolysis liquor of kraft-based dissolving pulp production process", Bioresource Technology, 102 (2011) 5177-5182.
Shi et.al., "A process for isolating lignin of pre-hydrolysis liquor of kraft pulping process based on surfactant and calcium oxide treatments", Biochemical Engineering Journal, 68 (2012) 19-24.
Shi et.al., "Optimizing the Poly Ethylene Oxide Flocculation Process for Isolating Lignin of Prehydrolysis Liquor of a Kraft-Based Dissolving Pulp Production Process", Ind. Eng. Chem. Res., (2012) 51, 5330-5335.
Sipos et.al., "Mechanism of the Positive effect of poly(ethylene glycol) addition in enzymatic hydrolysis of steam pretreated lignocelluloses", C.R. Biologies 334 (2011) 812-823.
Taherzadeh et.al., "Enzyme Based Hydroloysis Processes for Ethanol from Lignocellulosic Materials: A Review", BioResources, (2007) 2(4), 707-738.
Thring et.al., "Recovery of a Solvolytic Lignin: Effects of Spent Liquor/Acid Volume Ratio, Acid Concentration and Temperature", Biomass 23 (1990) 289-305.
Tu et.al., "Potential Enzyme Cost Reduction with the Addition of Surfactant during the Hydrolysis of Pretreated Softwood", Appl Biochem Biotechnol (2010) 161:274-287.
Tu et.al., "Evaluating the Distribution of Cellulases and the Recycling of Free Cellulases during the Hydrolysis of Lignocellulosic Substrates", Biotechnol. Prog. (2007) 23, 398-406.
Tu et.al., "Recycling Cellulases during the Hydrolysis of Steam Exploded and Ethanol Pretreated Lodgepole Pine", Biotechnol. Prog. (2007) 23, 1130-1137.
Van De Ven, "Association-induced polymer bridging by poly(ethylene oxide)—cofactor flocculation systems", Advances in Colloid and Interface Science 114-115 (2005) 147-157.
Wu et.al., "Flocculation of papermaking fines by poly(ethylene oxide) and various cofactors: Effects of PEO entanglement, salt and fines properties", Colloids and Surfaces A: Physicochem. Eng. Aspects 303 (2007) 211-218.
Xue et.al., "Strategies to Recycle Enzymes and their Impact on Enzymatic Hydrolysis for Bioethanol Production", BioResources (2012) 7(1) 602-615.
Liu et al., "Lignocellulosic ethanol production by starch-base industrial yeast under PEG detoxification", Scientific Reports, 6:20361,

(56) References Cited

OTHER PUBLICATIONS pp. 1-11, downloaded from https://media.nature.com/original/nature-assets/srep/2016/160203/srep20361/extref/srep20361-s1.pdf, on Jan. 5, 2018.

* cited by examiner

PROCESS FOR HYDROLYZING A PRETREATED FEEDSTOCK AND RECOVERING LIGNIN

This application is a national stage application of PCT/CA2014/051166 having an international filing date of Dec. 4, 2014, which claims benefit of U.S. provisional application No. 61/912,710 filed Dec. 6, 2013, U.S. provisional application No. 61/912,713 filed Dec. 6, 2013, and U.S. provisional application No. 61/912,724 filed Dec. 6, 2013, each of which is incorporated by reference herein.

TECHNICAL FIELD

The present invention relates to an improved process for hydrolyzing a pretreated lignocellulosic feedstock. In particular, the present invention relates to an improved process for hydrolyzing a pretreated lignocellulosic feedstock with at least cellulase enzymes to produce sugar.

BACKGROUND OF THE INVENTION

Lignocellulosic feedstock is a term commonly used to describe plant-derived biomass comprising cellulose, hemicellulose and lignin. Much attention and effort has been applied in recent years to the production of fuels and chemicals, primarily ethanol, from lignocellulosic feedstocks, such as agricultural wastes and forestry wastes, due to their low cost and wide availability. These agricultural and forestry wastes are typically burned or land-filled. Thus, using these lignocellulosic feedstocks for ethanol production offers an attractive alternative to disposal.

The first chemical processing step for converting lignocellulosic feedstock to ethanol, or other fermentation products, involves breaking down the fibrous lignocellulosic material to liberate sugar monomers from the feedstock for conversion to a fermentation product in a subsequent step of fermentation.

There are various known methods for producing fermentable sugars from lignocellulosic feedstocks, the most prominent one involving an acid or alkali pretreatment followed by hydrolysis of cellulose with cellulase enzymes and β-glucosidase. The purpose of the pretreatment is to increase the cellulose surface area and convert the fibrous feedstock to a muddy texture, with limited conversion of the cellulose to glucose. Acid pretreatment typically hydrolyses the hemicellulose component of the feedstock to yield xylose, glucose, galactose, mannose and arabinose and this is thought to improve the accessibility of the cellulose to cellulase enzymes. The cellulase enzymes hydrolyse cellulose to cellobiose which is then hydrolysed to glucose by β-glucosidase. Hydrolysis of the cellulose and hemicellulose can also be achieved with a single-step chemical treatment in which the lignocellulosic feedstock is contacted with a strong acid or alkali under conditions sufficient to hydrolyse both the cellulose and hemicellulose components of the feedstock to sugar monomers.

After production of a stream comprising fermentable sugar from the lignocellulosic feedstock, the sugars are fermented to ethanol or other fermentation products. If glucose is the predominant substrate present, the fermentation is typically carried out with a Saccharomyces spp. yeast that converts this sugar and other hexose sugars present to ethanol. However, glucose can also be fermented to other commercial products including lactic acid, sorbitol, acetic acid, citric acid, ascorbic acid, propanediol, butanediol, xylitol, acetone and butanol. This conversion can be carried out by a variety of organisms, including Saccharomyces spp.

One significant problem with enzymatic hydrolysis processes is the large amount of cellulase enzyme required, which increases the cost of the process. The cost of cellulase accounts for more than 50% of the cost of hydrolysis. There are several factors that contribute to the enzyme requirement, but one of particular significance is the presence of compounds that reduce the reaction rate of cellulases and/or microorganisms in the subsequent fermentation of the sugar. These compounds can also inhibit yeast, which decreases ethanol production and consequently makes the process more costly. Although the effects of inhibitors can be reduced by performing the hydrolysis at a more dilute concentration, this requires the use of a large hydrolysis reactor, which adds to the expense of the process.

One class of inhibitors released during the process are soluble inhibitors such as furfural, hydroxymethyl furfural, furan derivatives, organic acids, such as acetic acid and soluble phenolic compounds derived from lignin. Further examples of soluble inhibitors are glucose and cellobiose, which cause end-product inhibition on cellulases and beta-glucosidase, respectively.

Lignin is another inhibitor present in process streams in either soluble or insoluble form. Various groups have documented the negative effects of lignin on cellulase enzyme systems. Removal of lignin from hardwood (aspen) was shown to increase sugar yield by enzymatic hydrolysis (Kong et al., 1992, Applied Biochemistry and Biotechnology, 34/35:23-25). Similarly, removal of lignin from softwood was shown to improve enzymatic hydrolysis of the cellulose, an effect attributed to improved accessibility of the enzymes to the cellulose (Mooney et al., 1998, Bioresource Technology, 64:113-119). Other groups have demonstrated that cellulases purified from Trichoderma reesei bind to isolated lignin (Chernoglazov et al., 1988, Enzyme and Microbial Technology, 10(8):503-507) and have speculated on the role of the different binding domains in the enzyme-lignin interaction (Palonen et al., 2004, Journal of Biotechnology, 107:65-72). Binding to lignin and inactivation of Trichoderma reesei cellulases has been observed when lignin is added back to a pure cellulase system (Escoffier et al., 1991, Biotechnology and Bioengineering, 38(11):1308-1317).

A variety of methods have been suggested to reduce the negative impact of lignin on cellulases. Non-specific binding proteins (e.g. bovine serum albumin) have been shown to block interactions between cellulases and lignin surfaces (U.S. Publication Nos. 2004/0185542, U.S. Publication No. 2006/088922, WO 2005/024037 and WO 2009/429474). Other chemical blocking agents and surfactants have been shown to have a similar effect (U.S. Pat. Nos. 7,972,826 and 7,354,743). Yet another approach involves designing recombinant cellulases that are resistant to the inhibitory effects of lignin. Recombinant cellulases exhibiting reduced interactions or inactivation by lignin by genetic modification have been reported (WO 2010/096931).

A further approach to reduce the negative impact of lignin on the cellulase system involves removing lignin upstream of cellulase addition. Chang and Holtzapple (2000, Applied Biochemistry and Biotechnology, 84-86:5-37) examined the effects of acetic acid and lignin removal on the digestibility of poplar wood by cellulase enzymes. Cao et al. (1996, Biotechnology Letters, 18(9):1013-1018) disclose a method of steeping corn cobs with 2.9 M ammonium hydroxide for 24 hours at 26° C., which removed 80-90% of the lignin along with almost all the acetate from the feedstock.

Organosolv pretreatment is a further method to remove all or a portion of lignin upstream of enzymatic hydrolysis. This pretreatment involves the addition of organic solvents, such as ethanol, to lignocellulosic feedstock in order to extract the lignin.

Despite these efforts, there is a need for a more efficient process that comprises a step of carrying out enzymatic hydrolysis with cellulases. In particular, there is a need in the art to further reduce costs associated with such a process so as to make it more commercially viable.

SUMMARY OF THE INVENTION

The present invention may overcome one or more disadvantages of the prior art by taking into account the difficulties encountered in steps carried out during the processing of lignocellulosic feedstock to produce sugar for the production of a fermentation product such as ethanol. The process overcomes, ameliorates or provides useful alternatives in relation to known processes for carrying out such processes.

The invention is based on the discovery that recovering lignin in the form of lignin solids from a process stream can be improved by the addition of a polymer. According to one aspect of the invention, enzymatic hydrolysis of a pretreated lignocellulosic feedstock to produce glucose is carried out in the presence of cellulase enzymes and a polymer that binds or associates with lignin solids, thereby reducing the inhibitory effect of the polymer on the enzyme. The process further comprises conducting a solids-liquid separation to recover lignin solids from a process stream comprising lignin solids and the polymer. The process not only benefits from improvements in enzymatic hydrolysis, thus allowing for the reduction of enzyme dosage, but also improves the recovery of lignin solids.

The process stream from which the lignin solids are separated by the solids-liquid separation includes any stream arising from the process, or produced in subsequent steps, that comprises both the polymer and the lignin solids. The lignin solids are the undissolved solids of the process stream, as described further below. Process streams from which the lignin solids can be recovered include, without limitation, the hydrolyzed slurry comprising glucose and lignin solids, a fermentation beer or a still bottoms stream remaining after concentration of a fermentation product. The recovered lignin solids may then be used in fuel production or energy generation, for example by producing heat or electricity or to produce a lignin-based product, as described further herein.

In certain embodiments, the present invention can reduce the costs of solids-liquid separation. The inventors have recognized that the equipment used for solids-liquid separation of lignin solids, such as filtration, is large and capital intensive. Furthermore, the filtration is slow. Another problem recognized by the inventors is that the water content of the lignin solids resulting from the solids-liquid separation, particularly filtration, is undesirably high, which increases the cost of drying or burning the lignin. By conducting the solids-liquid separation in the presence of the polymer, the solids-liquid separation may occur more rapidly, require less water or filter aid and/or produce drier lignin solids.

In further embodiments of the invention, the process can also result in improved sugar recovery. It has become apparent to the inventors that the inefficiency in solids-liquid separation of lignin solids from process streams comprising sugar can reduce sugar yield by 4% or more. The yield loss of sugar in turn reduces the yield of ethanol or other fermentation products produced by the process. By carrying out the solids-liquid separation in the presence of the polymer, this sugar loss may be reduced. This in turn may increase the yield of fermentation product, such as ethanol, from the process.

The lignin solids may be separated from the process stream by filtration. The filtration may be selected from microfiltration, plate and frame filtration, cross-flow filtration, pressure flow filtration and vacuum filtration.

In another aspect, the invention is based on the recognition by the inventors that the addition of a polymer, such as a non-ionic polymer, to enzymatic hydrolysis using cellulases can improve cellulase enzyme performance, but that such additives are costly. This is particularly the case when they are used at the levels required on a commercial scale, such as between 2% and 20% on weight of undissolved pretreated solids. However, the addition of such polymers has the benefit that it can decrease the amount of cellulase enzyme required by potentially by as much as 60%. The invention provides processes to recover the polymer additives and re-use them within the process, thereby reducing the cost of the process. Thus, the process not only benefits from improvements in enzymatic hydrolysis, thus allowing for the reduction of enzyme dosage, but also improves its economic viability so that it can be implemented on a commercial scale.

Thus, according to various embodiments of this aspect of the invention, an enzymatic hydrolysis is conducted in the presence of a polymer, such as a non-ionic water soluble polymer. According to one embodiment of the invention, a significant proportion of the lignin from the incoming feedstock remains in the pretreated feedstock and is carried through to enzymatic hydrolysis with cellulase. The polymer binds or associates with the lignin solids as described hereinafter. The polymer is subsequently recovered from the lignin solids and re-used in the process. According to one aspect of the invention, there is provided a process for hydrolyzing a pretreated lignocellulosic feedstock in the presence of a polymer that binds or associates with lignin solids and recovering the polymer for use in the process comprising: (i) hydrolyzing the pretreated lignocellulosic feedstock with an enzyme mixture comprising at least cellulase enzymes to produce a hydrolyzed slurry comprising glucose and lignin solids, said hydrolyzing being conducted in the presence of the polymer that binds or associates with the lignin solids; (ii) obtaining a process stream comprising the polymer and the lignin solids; (iii) recovering the polymer from the lignin solids; and (iv) recycling the recovered polymer for use in the process.

As set out further below, the process stream from which the polymer can be recovered includes any stream arising from the process that contains both lignin solids and the polymer, including, without limitation, the hydrolyzed slurry comprising glucose and lignin solids, a fermentation beer or a still bottoms stream remaining after distillation. The lignin solids are the undissolved solids of the process stream, as set out further below.

In further embodiments of the invention there is provided processes for improving the recovery of polymer from process streams comprising lignin solids.

In an embodiment of the invention, the polymer that binds or associates with the lignin solids is recovered from the lignin solids by adding a chemical extractant to remove the polymer. The chemical extractant may be any suitable chemical that recovers the polymer, including but not limited to an alcohol or an alkali. The recovered polymer is recycled for use in the process. In one embodiment of the invention, the chemical extractant is recovered and re-used in the process.

In a further embodiment of the invention, the inventors have recognized that the addition of the chemical extractant can dissolve a portion of the lignin solids. It has further been recognized by the inventors that recycling a process stream comprising the polymer and additionally dissolved lignin within the process might have a negative impact on hydrolysis. If dissolved lignin is re-introduced to hydrolysis upon recycle, it may bind to or associate with the cellulase enzymes or the polymer, thereby decreasing the efficiency of the hydrolysis. In order to prevent or reduce any potential negative impact of dissolved lignin on the process, a process stream comprising lignin solids is treated with calcium hydroxide (lime) to maintain the lignin solids in this stream insoluble. This can reduce process risk associated with recycling dissolved lignin along with the polymer.

According to a further embodiment of the invention, there is provided a process for recycling the polymer within the process by heat treating a process stream comprising the polymer and lignin solids. It has been found that heat treatment increases binding or association of the polymer to lignin solids. As a result, a larger proportion of the polymer binds to the lignin solids and less of the polymer is present in the aqueous solution of a process stream. This can eliminate or reduce the requirement to recover the polymer from the aqueous solution, which in turn can decrease the capital cost of the process.

The inventors have further recognized that a portion of the polymer does not bind or associate with the lignin solids and thus remains in solution. Thus, in accordance with embodiments of the invention, the polymer in solution is recovered from the aqueous process stream and re-used in the process. Recovery of this proportion of the polymer added to the enzymatic hydrolysis has the potential to reduce the cost of cellulose hydrolysis with cellulase and improve the overall process economics.

Thus, also described herein is a process for hydrolyzing a pretreated lignocellulosic feedstock in the presence of a polymer and recovering at least a portion of the polymer for use in the process comprising: (i) hydrolyzing the pretreated lignocellulosic feedstock with an enzyme mixture comprising at least cellulase enzymes to produce a hydrolyzed slurry comprising glucose and lignin solids, said hydrolyzing being conducted in the presence of the polymer, wherein a portion of the polymer binds or associates with the lignin solids and a portion remains in solution; (ii) obtaining an aqueous process stream comprising the polymer that remains in solution; (iii) recovering the polymer from the aqueous process stream to obtain a recovered polymer; and (iv) recycling the recovered polymer for use in the process.

As set out further below, the aqueous process stream from which the polymer can be recovered includes any process stream arising from the process that contains polymer in solution. In an embodiment of the invention, the aqueous process stream is recovered by conducting a solids-liquid separation on a hydrolyzed slurry comprising glucose and lignin solids, a fermentation beer or a still bottoms stream remaining after distillation.

These and other features of the invention will become more apparent from the following description in which reference is made to the appended drawings.

DETAILED DESCRIPTION OF THE INVENTION

Description of Feedstock Types

Figure 1A:
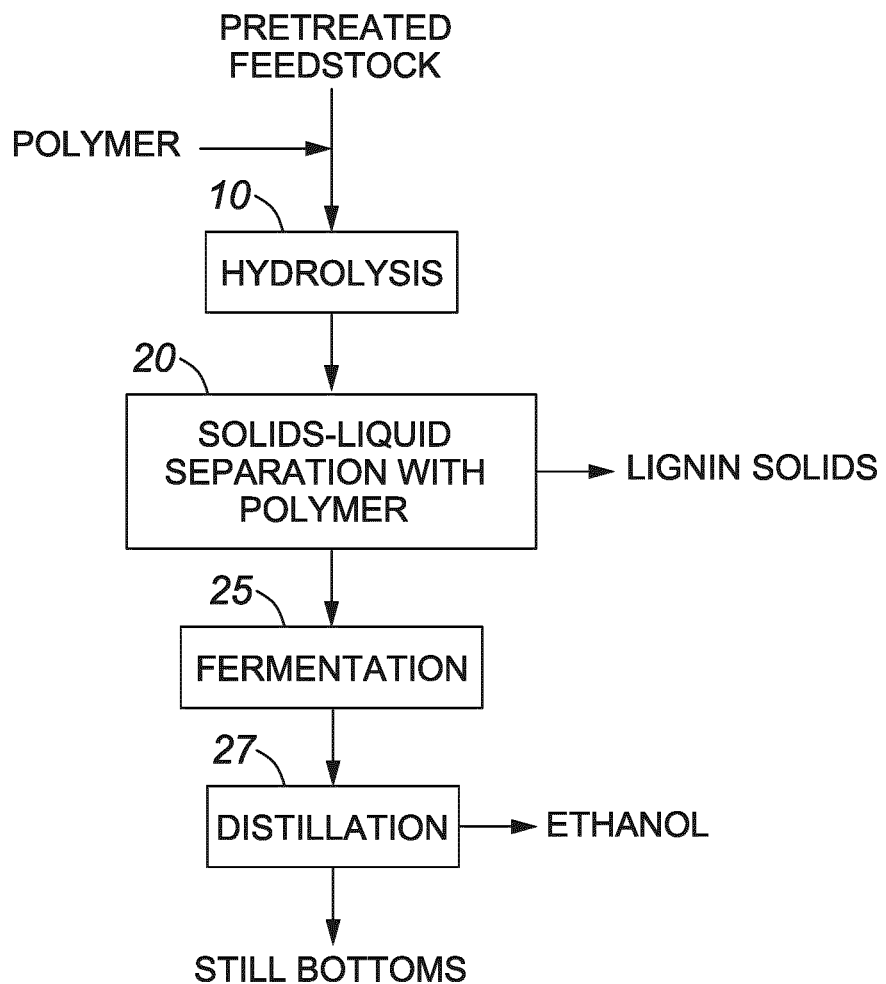
FIG. 1A shows a process in which a solids-liquid separation to recover lignin solids in the presence of polymer is performed on a hydrolyzed slurry resulting from hydrolyzing a pretreated lignocellulosic feedstock with cellulase enzymes.

By the term "lignocellulosic feedstock", it is meant any type of woody or non-woody plant biomass, or feedstock derived from plant biomass, such as, but not limited to, feedstock selected from:

(i) dedicated biomass crops such as, but not limited to grasses, for example, but not limited to, C4 grasses, such as switch grass, cord grass, rye grass, miscanthus, reed canary grass, or a combination thereof;

(ii) residues, byproducts or waste from the processing of plant biomass, or feedstock derived from plant biomass, in a facility to yield food or non-food products, for example, but not limited to, residues remaining after obtaining sugar from plant biomass such as sugar cane bagasse, sugar cane tops and leaves, beet pulp, or residues remaining after removing sugar from Jerusalem artichoke, or a combination thereof; and residues remaining after grain processing, such as corn fiber or corn stover;

(iii) agricultural residues, for example, but not limited to, soybean stover, corn stover, rice straw, sugar cane straw, rice hulls, barley straw, corn cobs, wheat straw, canola straw, oat straw, oat hulls, corn fiber, or a combination thereof;

(iv) forestry biomass for example, but not limited to, recycled wood pulp fiber, sawdust, hardwood, for example aspen wood, softwood, or a combination thereof;

(v) waste material derived from pulp and paper products such as newsprint, cardboard, or a combination thereof; and (vi) municipal waste.

Lignocellulosic feedstock may comprise one species of fiber or, alternatively, lignocellulosic feedstock may comprise a mixture of fibers that originate from different lignocellulosic feedstocks. In addition, the lignocellulosic feedstock may comprise fresh lignocellulosic feedstock, partially dried lignocellulosic feedstock, fully dried lignocellulosic feedstock, or a combination thereof. Moreover, new lignocellulosic feedstock varieties may be produced from any of those listed above by plant breeding or by genetic engineering.

Lignocellulosic feedstocks comprise cellulose in an amount greater than about 20%, more preferably greater than about 30%, more preferably greater than about 40% (w/w). For example, the lignocellulosic material may comprise from about 20% to about 50% (w/w) cellulose, or any amount therebetween. Furthermore, the lignocellulosic feedstock comprises lignin in an amount greater than about 10%, more typically in an amount greater than about 15% (w/w). Preferably, the lignocellulosic feedstock comprises about 20% to about 45% (w/w) cellulose, about 15% to about 35% (w/w) xylan and about 10% to about 25% (w/w) lignin. The lignocellulosic feedstock may also comprise sucrose, fructose and starch. Without being limiting, the amount of sucrose, fructose or starch present in lignocellulosic feedstocks is generally less than cellulose and xylan.

The fermentable sugar for the process may be partially derived from sugar and starch crops including, but not limited to, wheat, corn, sugar beets and sugar cane. Methods for producing fermentable sugar from such feedstocks are well known.

Feedstock Size Reduction

The lignocellulosic feedstock may be first subjected to size reduction by methods including, but not limited to, milling, grinding, agitation, shredding, compression/expansion, or other types of mechanical action. As would be appreciated by those of ordinary skill in the art, lignocellulosic feedstock that has been subjected to size reduction comprises feedstock particles having a range of lengths. In an embodiment of the invention, at least 90% by weight of the particles in the size reduced lignocellulosic feedstock have a length less than between about 1/8 and about 6 inches.

Size reduction by mechanical action can be performed by any type of equipment adapted for the purpose, for example, but not limited to, hammer mills, tub-grinders, roll presses, refiners, shredders and hydrapulpers. If size reduction is required, it can be performed while the lignocellulosic feedstock is dry or moist, i.e., having a moisture content of 0% to 20%, or while water is added to the lignocellulosic feedstock. Dry shredding can be carried out, for example, with an SSI or Grizzly shredder, hammer mill or tub grinder, while wet shredding may be performed with pulpers. When dry shredding is employed, the particle size may be between 1/2 to 6 inches. When hammer milling, the particle size may be less than 4 inches to less than 1/2 inch depending on the size of the screens used in the hammer mill. It should be appreciated that the lignocellulosic feedstock need not be subjected to size reduction if the particle size of the feedstock is already between 1/8 to 6 inches.

As discussed hereinafter, when the lignocellulosic feedstock particles are mixed with liquid the resultant mass is often characterized as a feedstock slurry. The feedstock slurry may be processed in equipment typically used to process liquid streams. A person of ordinary skill in the art could select a concentration of feedstock particles and particle characteristics that allows for ease of processing and that achieves a desired reactivity of the feedstock in pretreatment.

For the purposes of this specification, the size of the feedstock particles is determined by image analysis using techniques known to those of ordinary skill in the art. An example of a suitable image analysis technique is disclosed in Igathinathane (Sieveless particle size distribution analysis of particulate materials through computer vision, Computers and Electronics in Agriculture, 2009, 66:147-158), which reports particle size analyses of several different hammer milled feedstocks. The measurement may be a volume or a weight average length.

Washing of the feedstock may be carried out to remove sand, grit and other foreign particles as they can cause damage to the downstream equipment.

Feedstock Slurry Preparation

Slurrying of the feedstock may be carried out so that the feedstock can be pumped more readily. Slurrying may be carried out in any suitable batch or continuous mixing vessel, including a standpipe or pulper. Slurrying may be distinct from the water and chemical addition or may occur simultaneously therewith.

Slurrying can produce a feedstock slurry having any suitable undissolved solids content selected by those of ordinary skill in the art. The undissolved solids content of the feedstock slurry utilized may depend on the specific mixing means employed and the specific pumps used. In one embodiment of the invention, the undissolved solids content of the feedstock slurry is between about 2 wt % and about 40 wt % or more typically between about 4 wt % and about 30 wt %.

The undissolved solids content (UDS) is a weight ratio of dry solids to liquid in a process stream. The undissolved solids content in a process stream or any other solution or slurry described herein is arrived at by determining the weight of a sample and then filtering the sample through filter paper and washing with water to isolate the undissolved solids. The isolated undissolved solids are dried overnight at 105° C., preferably in an aluminum drying dish, and then weighed. The undissolved solids content is quantified by determining, as a percent, the number of grams of dry solids per gram of process stream or other solution.

The lignocellulosic feedstock contains leachable minerals, such as potassium, sodium, calcium and, in some instances, magnesium. The feedstock is optionally leached prior to pretreatment to remove these substances from the feedstock. By leaching the lignocellulosic feedstock, the level of compounds that increase acid demand during dilute acid pretreatment is reduced.

After slurrying, leaching and/or soaking, the lignocellulosic feedstock may optionally be dewatered by any suitable technique known to those of ordinary skill in the art. For instance, dewatering may be carried out by utilizing devices that remove water under pressure from the lignocellulosic feedstock slurry. Dewatering devices suitable for use in the invention includes pressurized screw presses, such as those described in WO 2010/022511 (incorporated herein by reference) and pressurized filters. The dewatering process optionally includes a pre-draining zone in order to drain out water from the feedstock slurry at atmospheric pressure or higher. This dewatered feedstock slurry is then sent to one or more devices for dewatering the slurry under pressure.

Water expressed from the lignocellulosic feedstock by the dewatering step may be reused in the process.

The feedstock slurry may be fed to the pressurized dewatering device via one or more high pressure pumps, such as those available from Sulzer Corp. or Andritz AG, or by other suitable feeding device. The pump or other feeding device increases the pressure of the feedstock slurry to e.g., about 70 psia to about 900 psia. The pressure may be measured with a pressure sensor located at the inlet on the dewatering device.

Pretreatment of the Lignocellulosic Feedstock

The term "pretreatment" or "pretreat" means a process in which the lignocellulosic feedstock is reacted under conditions that disrupt the fiber structure and that increase the susceptibility or accessibility of cellulose within the cellulosic fibers for subsequent enzymatic hydrolysis.

The pretreatment of lignocellulosic feedstock may be conducted with heat, by mechanical processing, addition of one or more chemicals, or any combination of such methods in order to increase the susceptibility or accessibility of the cellulose to enzymatic hydrolysis. According to an embodiment of the invention, the pretreatment involves contacting the lignocellulosic feedstock with one or more chemicals. In a further embodiment of the invention, the pretreatment is with acid, alkali or a hydrothermal pretreatment as set out below.

By the term "pretreated lignocellulosic feedstock" or "pretreated feedstock", it is meant a lignocellulosic feedstock that has been subjected to pretreatment so that the cellulose contained in the cellulosic fibers has an increased susceptibility or accessibility to subsequent enzymatic or chemical conversion steps. The pretreated feedstock contains cellulose that was present in the feedstock prior to pretreatment. In some embodiments, at least a portion of the xylan contained in the lignocellulosic feedstock is hydrolyzed to produce at least xylose in a pretreatment. The pretreated lignocellulosic feedstock may be a slurry. The pretreated lignocellulosic feedstock may be subjected to a solids-liquid separation and/or a washing step to remove a liquid portion, as described in more detail herein.

The pretreatment may be performed so that hydrolysis of the xylan occurs, such as between 70 and 100 wt % is hydrolyzed. In a further embodiment, between about 3 and about 15 wt % of the cellulose is hydrolyzed during pretreatment.

As well, some dissolution of the lignin in the feedstock may occur; for example from 0% to 25 wt % of the lignin may be dissolved during the pretreatment or during any preliminary treatment stages conducted prior to pretreatment such as alkali treatment (see WO 2012/019305). Thus, according to an embodiment of the invention from 0% to 25 wt % of the lignin by weight is dissolved during or before the pretreatment, or between 0% and 15 wt % lignin.

According to another embodiment of the invention, the pretreatment is carried out so that between about 50 wt % and 100 wt %, or between about 60 wt % and 100 wt %, or between about 70 wt % and 100 wt %, or between about 80 wt % and 100 wt % or between about 85 and 100 wt % of the lignin in the original lignocellulosic feedstock remains in the pretreated lignocellulosic feedstock after pretreatment.

If acid pretreatment is conducted, it is most advantageously carried out at a maximum temperature of about 160° C. to about 280° C. It should be understood that, in practice, there will be a time delay in the pretreatment process before the feedstock reaches this temperature range. Thus, the above temperatures correspond to those values reached after sufficient application of heat to reach a temperature within this range. The time that the feedstock is held at this temperature may be about 6 seconds to about 3600 seconds, or about 15 seconds to about 750 seconds or about 30 seconds to about 240 seconds.

The pretreatment is typically carried out under pressure. For example, the pressure during pretreatment may be between about 50 and about 700 psig or between about 75 and about 600 psig, or any pressure range therebetween.

The feedstock may be heated with steam during or prior to pretreatment. Without being limiting, one method to carry this out is to use low pressure steam to partially heat the feedstock, which is then pumped to a heating train of several stages. Other methods may be employed to heat the feedstock, such as commercially available mixing devices designed for introducing steam and optionally acid through spray nozzles as disclosed in WO 2013/040702.

The initial pH of the feedstock after acid addition may be between pH 0 and 4 or between pH 1 and 3.5. The acid pretreatment may be conducted with sulfuric acid, acetic acid, sulfur dioxide, phosphoric acid or a mixture thereof.

The acid pretreatment produces an acid pretreated feedstock. Sugars produced by the hydrolysis of hemicellulose during acid pretreatment are generally present in the composition and include xylose, glucose, arabinose, mannose, galactose or a combination thereof. Organic acids may be present in the acid pretreated feedstock as well and may include acetic acid, galacturonic acid, formic acid, lactic acid, glucuronic acid or a combination thereof. Many lignocellulosic feedstocks contain hemicellulose with acetyl groups attached to xylan. Pretreatment processes liberate acetic acid from the acetyl groups. This includes pretreatment with the application of heat without or with low levels of chemical addition as set out below.

According to one exemplary embodiment of the invention, the soluble components of the pretreated feedstock are separated from the solids. This separation may be carried out by washing the pretreated feedstock with an aqueous solution to produce a wash stream, and a solids stream comprising the pretreated feedstock. Alternatively, the soluble component is separated from the solids by subjecting the pretreated feedstock composition to a solids-liquid separation, using methods such as centrifugation, filtration or sedimentation. Optionally, a washing step may be incorporated into the solids-liquids separation. The separated solids, which contain pretreated feedstock, may then be fed to enzymatic hydrolysis with cellulase enzymes in order to convert the cellulose to glucose. The enzymatic hydrolysis of cellulose using cellulase enzymes is described in more detail hereinafter. The aqueous stream, which includes the sugars released during pretreatment, the pretreatment chemical and other soluble components, may then be fermented using a microorganism capable of fermenting the sugars derived from the hemicellulose component of the feedstock.

Pretreatment may also be carried out under alkaline conditions. The initial pH of the feedstock after alkali addition is greater than pH 8. Alkali pretreatment chemicals include sodium hydroxide, calcium hydroxide, potassium hydroxide, sodium carbonate, or mixtures thereof. Examples of suitable alkaline pretreatment processes include ammonia fiber expansion (AFEX) or dilute ammonia pretreatment.

According to the AFEX process, the lignocellulosic feedstock is contacted with ammonia or ammonium hydroxide, which is typically concentrated, in a pressure vessel. The contact is maintained for a sufficient time to enable the ammonia or ammonium hydroxide to swell (i.e., decrystallize) the cellulose fibers. The pressure is then rapidly reduced which allows the ammonia to flash or boil and explode the cellulose fiber structure. The flashed ammonia may then be recovered according to known processes. The AFEX process may be run at about 20° C. to about 150° C. or at about 20° C. to about 100° C. and all temperatures therebetween. The duration of this pretreatment may be about 1 minute to about 20 minutes, or any time therebetween.

Dilute ammonia pretreatment utilizes more dilute solutions of ammonia or ammonium hydroxide than AFEX. Such a pretreatment process may or may not produce any monosaccharides. Dilute ammonia pretreatment may be conducted at a temperature of about 100 to about 150° C. or any temperature therebetween. The duration for such a pretreatment may be about 1 minute to about 20 minutes, or any time therebetween.

As set out previously, many lignocellulosic feedstocks contain hemicellulose with acetyl groups attached to xylan. Exposure of the lignocellulosic feedstock to elevated temperatures liberates acetic acid from the acetyl groups. The acetic acid and optionally other organic acids released from the feedstock under elevated temperature may hydrolyze a portion of the xylan in the lignocellulosic feedstock and thus may function to pretreat the feedstock. Such pretreatment carried out without the addition of pretreatment chemical or with addition of a lower than conventional concentration of acid or alkali or other chemical such that the initial pH of the feedstock is between about 4 and about 8, is referred to as "hydrothermal pretreatment". An example of a suitable temperature for hydrothermal pretreatment is between about 80° C. and about 260° C., or between about 100° C. and about 210° C.

Subsequent to pretreatment, the pretreated feedstock is typically cooled to decrease its temperature to a range at which the cellulase enzymes are active. It should be appreciated that cooling of the feedstock can occur in a number of stages utilizing flashing, heat exchange or other suitable techniques.

The undissolved solids content in the pretreated feedstock depends on the particle size, water retention, pump capacity and other properties of the feedstock. Typically, the undissolved solids content is between about 3% and 40% (w/w), between about 5% and about 35% (w/w), or between about 8% and about 30% (w/w) or any amount therebetween. Optionally, the undissolved solids content is increased to a desired level by dewatering of the feedstock slurry prior to pretreatment, for example as set forth in WO 2010/022511 (incorporated herein by reference).

Enzymatic Hydrolysis

After pretreatment, the resultant pretreated lignocellulosic feedstock is hydrolyzed with an enzyme mixture comprising at least cellulase enzymes to produce a hydrolyzed slurry comprising glucose and lignin solids. The hydrolysis is conducted in the presence of a polymer that binds or associates with the lignin solids. The presence of the polymer during hydrolysis of the pretreated lignocellulosic feedstock is thought to improve the hydrolysis of cellulose by binding or associating with lignin solids, thereby preventing non-productive binding of the cellulase to lignin solids. Further, this interaction may be responsible for facilitating separation of lignin solids from a process stream by a solids-liquid separation.

The polymer used in the process of the invention also improves a solids-liquid separation to recover lignin solids from a process stream comprising same. The improvement may be determined by measuring the time required to remove a volume of liquid, such as water, from the lignin solids by the solids-liquid separation in both the presence and absence of the polymer under otherwise identical conditions. The presence of polymer during the solids-liquid separation may increase the rate of the solids-liquid separation by at least 1.5-fold to 12-fold, by 2-fold to 10-fold or by 2.5-fold to 8-fold relative to the absence of polymer addition under otherwise identical conditions. In an embodiment of the invention, such improvements are realized by carrying out filtration.

The polymer may be added at any point in the process prior to the solids-liquid separation or enzymatic hydrolysis, such as to the lignocellulosic feedstock prior to or during pretreatment, to the pretreated feedstock, at any stage during enzymatic hydrolysis with cellulase, or a combination thereof. According to an embodiment of the invention, the polymer is added to the pretreated feedstock or during any stage of enzymatic hydrolysis with cellulase, or a combination thereof.

The quantity of polymer present during hydrolysis may be between 2 wt % and 20 wt %, or between 2 wt % and 15 wt %, or between about 2 wt % and 10 wt % on weight of undissolved pretreated solids. The polymer can be added directly as a solid or liquid, or in a slurry or solution with water. Determination of the weight of undissolved pretreated solids involves obtaining a sample of pretreated feedstock and then filtering the sample through filter paper while washing with water to isolate the undissolved pretreated solids. The undissolved pretreated solids that are isolated are dried, typically overnight, at 105° C. and then weighed. The determination of undissolved pretreated solids is performed on the pretreated feedstock prior to its hydrolysis with cellulase enzymes.

By "binds or associates", it is meant that at least 10 mg of polymer/g lignin solids is associated or bound to lignin solids after incubation with lignin solids at 50° C. for 2 hours. The amount of polymer that binds or associates with lignin solids in mg of polymer/g lignin solids involves adding a defined amount of polymer to a sample comprising lignin solids and determining the concentration of polymer in solution after incubation at 50° C. for 2 hours and subtracting this value from the amount of polymer added to arrive at the amount of polymer bound or associated with the lignin solids. Such a procedure is set forth in Example 1. In an embodiment of the invention, the amount of polymer that binds or associates with the lignin solids is between 10 and 90 mg of polymer/g lignin solids, between 15 and 80 mg of polymer/g lignin solids or between 20 and 70 mg of polymer/g lignin solids.

Without being bound by theory, the polymer may interact with lignin solids by, for example, a non-covalent, intermolecular attraction, such as dipole-dipole forces, van der Waals forces, or a combination thereof. Such non-covalent, intermolecular attractions may include hydrogen bonding, hydrophobic interaction, or any combination thereof.

For example, non-ionic polymers comprising repeating units of ethylene oxide ($CH_2CH_2O$) may interact with lignin solids via hydrophobic interaction and/or hydrogen bonding. Lignin may comprise both phenolic and aliphatic hydroxyl groups that may participate in hydrogen bonding with the ether groups in polyethylene oxide. The $CH_2$ groups in ethylene oxide units of polyethylene glycol chains may interact with hydrophobic parts of lignin.

Examples of polymers included within the scope of the invention include non-ionic polymers. The non-ionic polymer is typically "water soluble", which means that it has a solubility of at least 10 g/L in solution at 50° C., preferably greater than 25 g/L. In a further embodiment of the invention, the polymer has an octanol-water partition coefficient (P) of −2.0 to −4.0. The octanol-water partition coefficient is described by Sangster Research Laboratories, Montreal, online: LOGKOW, A databank of evaluated octanol-water partition coefficients (Log P), http://logkow.cisti.nrc.ca/logkow/index.jsp and Sangster, 1989, J. Phys. Chem. Ref. Data, 18(3):1111-1117.

In an embodiment of the invention, the polymer is a non-ionic, water soluble polymer including a polyvinyl alcohol, a polyvinyl pyrolidone, or a polyether including aromatic polyethers and aliphatic polyethers. By the term "polyether", it is meant a polymer that comprises an ether functional group in its main chain or backbone. According to a further embodiment of the invention, the polymer is a polyether such as an aromatic polyether or an aliphatic polyether. Preferably, the polymer is an aliphatic polyether selected from paraformaldehyde, polyethylene glycol, polypropylene glycol, poly(tetramethylene ether) glycol, paraformaldehyde or mixtures thereof. Examples of commercially available polyethylene glycol include Carbowax®, Lutrol®, Pluracol®, Droxol®, Emery®, Nopalcol®, Rhodasurf® and Teric®.

In a further embodiment of the invention, the polymer comprises repeating units of ethylene oxide ($CH_2CH_2O$), propylene oxide ($CH_3CHCH_2O$) or a combination thereof. Preferably, the polymer comprises repeating units of ethylene oxide ($CH_2CH_2O$).

The non-ionic polymer may also be a non-ionic surfactant. This includes co-polymers that are amphiphilic, meaning they comprise hydrophobic and hydrophilic regions or blocks. Non-limiting examples include Lutensol® AT-80, Tween® 20, Tween® 40, Tween® 80, Triton™ X-100, Triton™ X-114, Agrimul® and hydrophobically modified ethylene oxide/propylene oxide co-polymer (HM-EOPO).

The water-soluble polymer may be a surfactant comprising a polyether. Examples of amphiphilic block co-polymers include non-ionic surfactants comprising a polyether region or block, including a substituted polyether. An example is a block co-polymer comprising polyethylene glycol. Non-limiting examples include conjugates of Tween® and polyethylene glycol. In further embodiments of the invention, the water-soluble polymer is a protein comprising a polyether, such as a conjugate of casein and polyethylene glycol. Other examples include polysorbate and derivatives thereof.

The molecular weight of the polymer may be between 100 and 100,000 Da or between about 1,000 and 15,000 Da, between 1,500 and 12,000 Da or between 3,000 and 10,000 Da.

The enzymatic hydrolysis of the cellulose to soluble sugars can be carried out with any type of cellulase enzymes suitable for such purpose and effective at the pH and other conditions utilized, regardless of their source. Among the most widely studied, characterized and commercially produced cellulases are those obtained from fungi of the genera *Aspergillus, Humicola, Chrysosporium, Melanocarpus, Myceliopthora, Sporotrichum* and *Trichoderma*, and from the bacteria of the genera *Bacillus* and *Thermobifida*. Cellulase produced by the filamentous fungi *Trichoderma longibrachiatum* comprises at least two cellobiohydrolase enzymes termed CBHI and CBHII and at least four EG enzymes. As well, EGI, EGII, EGIII, EG V and EGVI cellulases have been isolated from *Humicola insolens* (see Lynd et al., 2002, Microbiology and Molecular Biology Reviews, 66(3):506-577 for a review of cellulase enzyme systems and Coutinho and Henrissat, 1999, "Carbohydrate-active enzymes: an integrated database approach." In Recent Advances in Carbohydrate Bioengineering, Gilbert, Davies, Henrissat and Svensson eds., The Royal Society of Chemistry, Cambridge, pp. 3-12, each of which are incorporated herein by reference).

An appropriate cellulase dosage can be about 1.0 to about 40.0 mg of protein per gram of cellulose, or any amount therebetween. The protein concentration can be measured according to Smith et al., 1985, Anal Biochem. 150(1):76-85; which is incorporated herein by reference). A preferred cellulase dosage is about 1 to 15 mg per gram cellulose.

The conversion of cellobiose to glucose is carried out by the enzyme β-glucosidase. By the term "β-glucosidase", it is meant any enzyme that hydrolyzes the glucose dimer, cellobiose, to glucose. The activity of the β-glucosidase enzyme is defined by its activity by the Enzyme Commission as EC#3.2.1.21. The β-glucosidase enzyme may come from various sources; however, in all cases, the β-glucosidase enzyme can hydrolyze cellobiose to glucose. The β-glucosidase enzyme may be a Family 1 or Family 3 glycoside hydrolase, although other family members may be used in the practice of this invention. The preferred β-glucosidase enzyme for use in this invention is the Bgl1 protein from *Trichoderma reesei*. It is also contemplated that the β-glucosidase enzyme may be modified to include a cellulose binding domain, thereby allowing this enzyme to bind to cellulose.

The enzymatic hydrolysis is generally conducted at a pH between about 4.0 and 6.0 as this is within the optimal pH range of most cellulases. If acid pretreatment is utilized, the pH of the feedstock will be increased with alkali to about pH 4.0 to about 6.0 prior to enzymatic hydrolysis, or more typically between about 4.5 and about 5.5. However, cellulases with pH optima at more acidic and more alkaline pH values are known.

The alkali can be added to the pretreated feedstock after it is cooled, before cooling, or at points both before and after cooling. The alkali may be added in-line to the pretreated feedstock, such as an in-line dispersion device described previously, to a pump downstream of pretreatment or directly to a hydrolysis vessel. The point of alkali addition can coincide with the cellulase enzyme addition, or it can be added upstream or downstream of the location of the enzyme addition.

The temperature of the slurry is adjusted so that it is within the optimum range for the activity of the cellulase enzymes. Generally, a temperature of about 45° C. to about 70° C., or about 45° C. to about 65° C., or any temperature therebetween, is suitable for most cellulase enzymes. However, the temperature of the slurry may be higher for thermophilic cellulase enzymes.

In order to maintain the desired hydrolysis temperature, the hydrolysis reactors may be jacketed with steam, hot water, or other heat sources. Moreover the reactors may be insulated to retain heat.

It is preferred that enzymatic hydrolysis and fermentation are conducted in separate vessels so that each biological reaction can occur at its respective optimal temperature. However, the hydrolysis may be conducted simultaneously with fermentation in a simultaneous saccharification and fermentation. SSF is typically carried out at temperatures of 35-38° C., which is a compromise between the 50° C. optimum for cellulase and the 28° C. optimum for yeast. Consequently, this intermediate temperature can lead to substandard performance by both the cellulase enzymes and the yeast.

Other design parameters of the hydrolysis system may be adjusted as required. For example, the volume of a hydrolysis reactor in a hydrolysis system with cellulase can range from about 100,000 L to about 5,000,000 L, or any volume therebetween, for example, between 200,000 and 750,000 L, or any amount therebetween, although reactors of small volume may be preferred to reduce cost. The total residence time of the slurry in a hydrolysis system may be between about 12 hours to about 200 hours, or any amount therebetween. In continuous hydrolysis systems this represents the average residence time.

After the hydrolysis is complete, the product is a hydrolyzed slurry comprising glucose and lignin solids. Optionally, the hydrolyzed slurry further comprises sugars released during pretreatment, such as xylose, arabinose, mannose, galactose, or a combination thereof. Lignin in this process stream is present in insoluble form as part of the lignin solids and soluble form in which the lignin is dissolved in solution. The lignin solids are the undissolved solids content of the hydrolyzed slurry. In addition to lignin, the lignin solids may further comprise unhydrolyzed cellulose. Other compounds may make up the lignin solids as well, including insoluble ash and other insoluble inorganics; insoluble waxes; and other insoluble organics.

Lignin solids present in the hydrolyzed slurry, and optionally other insoluble solids, may be recovered using any suitable solids-liquid separation technique prior to any further processing. However, it may be desirable in some circumstances to carry forward the lignin solids in the hydrolyzed slurry for further processing. According to such embodiment, lignin solids are removed by a solids-liquid separation in a downstream process, such as after fermentation and prior to distillation or after distillation, as set forth below.

If the solids-liquid separation is carried out on a process stream that is the hydrolyzed slurry, lignin solids may be separated from the stream by centrifugation, sedimentation or filtration. The filtration may include microfiltration, plate and frame filtration, cross-flow filtration, pressure filtration or vacuum filtration. Optionally, a washing step may be incorporated into the solids-liquids separation.

As discussed, by carrying out the solids-liquid separation in the presence of the polymer, the sugar loss from the hydrolyzed slurry may be reduced. This in turn may increase the yield of fermentation product, such as ethanol, from the process. According to certain embodiments of the invention, the sugar loss is decreased by at least 50%, by at least 30%, by at least 20%, or by at least 10% relative to the same process conducted under the same conditions in the absence of any polymer addition.

In an embodiment of the invention, most or a significant portion of the hydrolyzed slurry is fed to the solids-liquid separation. The portion of the hydrolyzed slurry that is subjected to the solids-liquid separation to recover lignin solids may be between 50 wt % and 100 wt % of the slurry, or between 60 wt % and 100 wt % of the slurry or between 70 wt % and 100 wt % of the slurry.

Fermentation

Fermentation of glucose resulting from the hydrolysis may produce one or more of the fermentation products selected from an alcohol, a sugar alcohol, an organic acid and a combination thereof.

The fermentation is typically conducted at a pH between about 4.0 and about 6.0, or between about 4.5 and about 6.0. To attain the foregoing pH range for fermentation, it may be necessary to add alkali to a stream comprising glucose which is fed to the fermentation.

In one embodiment of the invention, the fermentation product is an alcohol, such as ethanol or butanol. For ethanol production, the fermentation may be carried out with a *Saccharomyces* spp. yeast or a *Zymomonas mobilis* bacteria. Glucose and any other hexoses present in the sugar stream may be fermented to ethanol by wild-type *Saccharomyces cerevisiae*, although genetically modified yeasts may be employed as well, as discussed below. The ethanol may then be distilled to obtain a concentrated ethanol solution. Butanol may be produced from glucose by a microorganism such as *Clostridium acetobutylicum* and then concentrated by distillation.

Xylose and arabinose that are derived from the hemicellulose may also be fermented to ethanol by a microbial strain that naturally contains, or has been engineered to contain, the ability to ferment these sugars to ethanol. Examples of microbes that have been genetically modified to ferment xylose include recombinant *Saccharomyces* strains into which has been inserted either (a) the xylose reductase (XR) and xylitol dehydrogenase (XDH) genes from *Pichia stipitis* (U.S. Pat. Nos. 5,789,210, 5,866,382, 6,582,944 and 7,527,927 and European Patent No. 450530) or (b) fungal or bacterial xylose isomerase (XI) gene (U.S. Pat. Nos. 6,475,768 and 7,622,284). Examples of yeasts that have been genetically modified to ferment L-arabinose include, but are not limited to, recombinant *Saccharomyces* strains into which genes from either fungal (U.S. Pat. No. 7,527,951) or bacterial (WO 2008/041840) arabinose metabolic pathways have been inserted.

Organic acids that may be produced during the fermentation include lactic acid, citric acid, ascorbic acid, malic acid, succinic acid, pyruvic acid, hydroxypropanoic acid, itaconoic acid and acetic acid. In a non-limiting example, lactic acid is the fermentation product of interest. The most well-known industrial microorganisms for lactic acid production from glucose are species of the genera *Lactobacillus, Bacillus* and *Rhizopus.*

Moreover, xylose and other pentose sugars may be fermented to xylitol by yeast strains selected from the group consisting of *Candida, Pichia, Pachysolen, Hansenula, Debaryomyces, Kluyveromyces* and *Saccharomyces*. Bacteria are also known to produce xylitol, including *Corynebacterium* sp., *Enterobacter liquefaciens* and *Mycobacterium smegmatis.*

In practice, the fermentation is typically performed at or near the temperature and pH optimum of the fermentation microorganism. A typical temperature range for the fermentation of glucose to ethanol using *Saccharomyces cerevisiae* is between about 25° C. and about 35° C., although the temperature may be higher if the yeast is naturally or genetically modified to be thermostable. The dose of the fermentation microorganism will depend on other factors, such as the activity of the fermentation microorganism, the desired fermentation time, the volume of the reactor and other parameters. It should be appreciated that these parameters may be adjusted as desired to achieve optimal fermentation conditions.

The fermentation may also be supplemented with additional nutrients required for the growth of the fermentation microorganism. For example, yeast extract, specific amino acids, phosphate, nitrogen sources, salts, trace elements and vitamins may be added to the hydrolyzate slurry to support their growth.

The fermentation may be conducted in batch, continuous or fed-batch modes with or without agitation. Preferably, the fermentation reactors are agitated lightly with mechanical agitation. A typical, commercial-scale fermentation may be conducted using multiple reactors. The fermentation microorganisms may be recycled back to the fermentor or may be sent to distillation without recycle. If lignin solids are not removed upstream of fermentation, yeast recycle is typically not carried out.

The fermentation results in a process stream referred to herein as "fermentation beer". The fermentation beer comprises the fermentation product such as an alcohol, a sugar alcohol or an organic acid, organic and inorganic components. Microorganisms are potentially present as well depending upon whether or not they are removed from the beer by filtration or other means prior distillation of the beer. The beer may additionally comprise components added during the fermentation to support growth of the microorganisms and/or any organics that have not been consumed by the microorganisms, along with soluble and insoluble inorganic salts.

The fermentation beer is a process stream arising from the process on which the solids-liquid separation may be conducted to recover lignin solids. This process stream will comprise lignin solids and the polymer if the lignin solids are not recovered upstream of fermentation. In this case, the fermentation beer will comprise both the polymer and lignin solids. Recovery of lignin solids from this process stream is described in more detail below.

Distillation

If ethanol or butanol is the fermentation product, the recovery is carried out by distillation, typically with further concentration of the product by molecular sieves or membrane extraction.

The fermentation beer that is sent to distillation is a dilute alcohol solution. The fermentation beer may comprise lignin solids that are part of an undissolved solids content of the beer, including unconverted cellulose, and any components added during the fermentation to support growth of the microorganisms.

Microorganisms are potentially present during the distillation depending upon whether or not they are recycled during the fermentation. The broth is preferably degassed to remove carbon dioxide and then pumped through one or more distillation columns to separate the alcohol from the other components in the broth. The mode of operation of the distillation system depends on whether the alcohol has a lower or a higher boiling point than water. Most often, the alcohol has a lower boiling point than water, as is the case when ethanol is distilled.

In those embodiments in which ethanol is concentrated, the column(s) in the distillation unit is preferably operated in a continuous mode, although it should be understood that batch processes are also encompassed by the present invention. Heat for the distillation process may be introduced at one or more points either by direct steam injection or indirectly via heat exchangers. The distillation unit may contain one or more separate beer and rectifying columns, in which case dilute beer is sent to the beer column where it is partially concentrated. From the beer column, the vapour goes to a rectification column for further purification. Alternatively, a distillation column is employed that comprises an integral enriching or rectification section.

After distillation, the water remaining may be removed from the vapour by a molecular sieve resin, by membrane extraction, or other methods known to those of skill in the art for concentration of ethanol beyond the 95% that is typically achieved by distillation. The vapour may then be condensed and denatured.

When the alcohol has a higher boiling point than water, such as butanol, the distillation is run to remove the water and other volatile compounds from the alcohol. The water vapor exits the top of the distillation column and is known as the "overhead stream".

A process stream remaining after distillation and containing solids, referred to herein as "still bottoms" or as a "still bottoms stream", is withdrawn from the bottom of one or more of the column(s) of a distillation unit. This process stream will contain lignin solids if they have not been recovered in an upstream stage of the process. The lignin solids from this stream may be recovered by a solids-liquid separation as described below.

Lignin Solids Recovery

The process stream from which lignin solids are recovered by the solids-liquid separation includes any stream arising from the process that comprises the lignin solids and the polymer. Optionally dissolved lignin is also present in this process stream. The lignin solids are the undissolved solids content of the process stream. In addition to lignin, the lignin solids content may further comprise unhydrolyzed cellulose. Other unhydrolyzed compounds may be part of the lignin solids content as well, depending on the source of the process stream.

As discussed, the process stream may include the hydrolyzed slurry comprising glucose and lignin solids. In a further embodiment, the process stream comprising lignin solids is a fermentation beer or the still bottoms stream remaining after distillation.

The undissolved solids content of the process stream on which the solids-liquid separation is conducted may be between 3 and 50 wt % or between 5 and 30 wt % or between 8 and 25 wt %. The undissolved solids content is measured by filtering, drying and weighing the solids, as described above.

The solids-liquid separation may be carried out by centrifugation, filtration or sedimentation. Optionally, a washing step may be incorporated into the solids-liquids separation.

In an embodiment of the invention, the solids-liquid separation is filtration. By way of example, the filtration may include microfiltration, plate and frame filtration, cross-flow filtration, pressure filtration or vacuum filtration.

Only a portion of the process stream comprising lignin solids and the polymer need be fed to the solids-liquid separation to recover lignin solids therefrom. However, it is preferable that most or a significant portion of the process stream is fed to the solids-liquid separation. In an embodiment of the invention, the portion of the process stream comprising lignin solids and the polymer that is fed to the solids-liquid separation to recover lignin solids therefrom may be between 50 wt % and 100 wt % of the process stream, or between 60 wt % and 100 wt % of the process stream or between 70 w % and 100 wt % of the process stream.

The solids-liquid separation may be carried out at a temperature of between 10° C. and 200° C., between 12° C. and 150° C. or between 15° C. and 100° C.

In an embodiment of the invention, the solids-liquid separation is carried out at elevated temperature as it has been found that the solids-liquid separation is more efficient when the temperature is raised. For example, the solids-liquid separation may be carried out at a temperature of between 25° C. and 200° C., between 30° C. and 200° C., between 40° C. and 200° C., between 45° C. and 200° C., between 50° C. and 200° C., between 55° C. and 200° C. or between 60° C. and 200° C. In a further embodiment of the invention, the solids-liquid separation is carried out on a still bottoms stream at these elevated temperature ranges. The undissolved solids content of the stream comprising recovered lignin solids resulting from the separation is typically greater than 20 wt %, more typically greater than 30 wt %.

In a non-limiting example, a particularly suitable device for recovery of lignin solids is a filter press. According to such embodiment, an incoming process stream comprising lignin, the polymer and other undissolved solids is fed to a feed tank and then pumped to the lignin press where dewatering occurs. A lignin cake is then obtained for use in fuel production or energy generation. Optionally, lignin solids may be isolated for use as a lignin-based product as described hereinafter.

If the solid-liquid separation is conducted using a filter press, the flux can be used to characterize the resistance of a filter cake, which is a method for measuring the performance of the filtration. The flux can be measured in volume/surface area of the filter press/hour, measured in units of $L/m^2/h$. In order to determine if a given polymer improves the performance of the filtration, the flux can be measured with and without the addition of polymer, under otherwise identical conditions. The improvement in flux due to the addition of polymer can then be measured as a percentage increase in flux. The percentage increase in flux can be at least 20%, at least 50% or at least 150%.

Recovery of the Polymer from Lignin Solids (a) Extraction of Polymer

After obtaining a process stream comprising the polymer and the lignin solids, such as from the solids-liquid separation, the polymer is recovered from the lignin solids. The undissolved solids content of the process stream from which the polymer is recovered from the lignin solids is typically between 20 wt % and 80 wt %, more typically between 30 wt % and 70 wt %.

Recovering the polymer from the lignin solids may comprise adding a chemical extractant, such as a liquid extractant, to recover the polymer from the lignin solids in an extraction step. The chemical extractant may be an alcohol or alkali. According to one exemplary embodiment of the invention, the chemical extractant is recovered and recycled for use in the extraction.

In one particularly advantageous embodiment of the invention, the extraction is with an alcohol. In such embodiments, the alcohol may be a short-chain aliphatic alcohol. For example, the alcohol may be a short-chain alcohol having an alkyl chain of 1-4 carbons. The alcohol may be selected from ethanol, methanol, propanol and butanol. In a further embodiment, the propanol is isopropanol, and the butanol is n-butanol.

The alcohols may be used in pure form (neat) or as an aqueous solution in water. The alcohol may also be present as a two-phase mixture comprising a water-rich phase and an alcohol-rich phase. An example of an alcohol that is present as a two-phase mixture is butanol at concentrations between about 7.3% and 78% in mixtures with water. Thus, in certain embodiments of the invention, the polymer is recovered from lignin solids by extraction with concentrated alcohol, an aqueous solution of an alcohol or a two-phase mixture of an alcohol-rich phase and a water rich-phase.

The extraction may be carried out at between −20° C. and 80° C., or between 4° C. and 80° C., or between 20° C. and 70° C., or between 30° C. and 60° C. The extraction may be carried out for 1 to 60 minutes, for 1 to 45 minutes or from 5 to 40 minutes. In an example of the invention, the extraction removes over 50%, over 60%, over 70%, more preferably over 90% of the polymer from the lignin by weight.

After the extraction, the liquid portion comprising the extractant, the extracted polymer, possibly water, and any dissolved lignin is separated from lignin solids by a solids-liquid separation. The solids-liquid separation may be filtration or centrifugation. The resulting liquid is referred to as the extractant liquid.

If an alcohol is the extractant, it may be recovered from the extractant liquid for example by flashing, evaporation or distillation. The alcohol may subsequently be condensed. The recovered condensed alcohol may be subsequently recycled back to the extraction.

After the alcohol is recovered from the extractant liquid, the remaining stream comprises the polymer and any water and lignin that has been carried into the extraction. A portion of the lignin that is dissolved in the extraction might precipitate upon removal of the extractant. It might be desirable to add water to this stream, also referred to herein as a "polymer stream" to permit better handling and/or pumping of this stream. The polymer stream can then be added back to the enzymatic hydrolysis process. This allows the polymer to be reused in the process, which overcomes the high cost of adding the polymer to the hydrolysis.

(b) Lime Addition

As discussed, the inventors have recognized that the addition of a chemical extractant can dissolve a portion of the lignin. For example, according to an embodiment of the invention, 5% to 30% or 10% to 25% of the lignin solids by weight are dissolved by the extraction. A portion of this lignin might precipitate upon removal of the extractant. It has further been recognized by the inventors that recycling the polymer stream comprising the polymer and additionally lignin within the process might have a negative impact on hydrolysis. If lignin is re-introduced to hydrolysis upon recycle, it may bind to or associate with the cellulase enzymes or the polymer, thereby decreasing the efficiency of the hydrolysis. In order to prevent or reduce any negative impact of lignin on the process due to recycle, a process stream comprising lignin solids is treated with calcium oxide or calcium hydroxide, collectively referred to as "lime" to maintain the lignin solids in insoluble form. This can reduce process risk associated with recycling lignin along with the polymer.

The lignin solids may be treated with lime before, during, or after the extraction of the polymer with the chemical extractant. If the lime treatment is prior to the extraction, the lignin is rendered insoluble during the extraction. If the lime treatment is after the extraction, the dissolved lignin is precipitated.

Typically the lime is prepared as a slurry in an aqueous solution. The lime may be added in sufficient quantity to a process stream comprising the polymer and lignin solids to achieve a pH between 8 and 12 or between 9 and 11. The treatment may be carried out at 20-80° C. for 10 minutes to 2 h.

When lime is added before or during extraction, the lignin does not dissolve significantly during the subsequent extraction. While not wishing to be bound by theory, it is believed that this effect is due to calcium binding to the lignin. By maintaining the lignin solids in insoluble form, the water soluble polymer can be recycled in the process with reduced levels of lignin.

When lime is added after extraction, it is added in sufficient volumes to precipitate dissolved lignin present after extraction. This forms precipitated lignin that can be separated from the soluble polymer that has been extracted. The precipitated lignin can be separated from the soluble polymer by any suitable solids-liquid separation.

(c) Heat Treatment

According to a further embodiment of the invention, there is provided a process for recycling the non-ionic polymer within the process by heat treating a process stream comprising the polymer and lignin solids. It has been found that heat treatment increases the amount of the polymer that is bound or associated with the lignin solids. As a result, a larger proportion of the polymer binds to the lignin solids and a lesser amount of the polymer is present in the aqueous solution of a process stream. This can increase the amount of the polymer recovered from the lignin solids, which in turn can decrease the capital cost of the process.

The heat treatment comprises raising the temperature of a process stream comprising polymer and lignin solids upstream of a step of recovering polymer from the lignin solids. The polymer is subsequently extracted and recovered for use in the process. The heat treatment is carried out prior to any solids-liquid separation step to recover polymer and lignin solids. Without being limiting, the process stream that is heated may be the hydrolyzed slurry or a fermentation beer.

The heat treatment may involve heating a process stream from 40° C. to 150° C., between 50° C. and 130° C. or between 65° C. and 120° C. The duration of the heat treatment may be between 1 and 60 minutes, between 5 and 50 minutes or between 10 and 30 minutes.

Conducting the heat treatment on the fermentation beer may involve exposing the lignin solids and polymer present in the fermentation beer to distillation. According to this embodiment, the lignin solids and polymer are carried through fermentation without any solids-liquid separation. The fermentation beer is then exposed to the temperatures at which distillation is carried out, which may be between 90° C. and 180° C. or between 90° C. and 125° C.

Recovery of Polymer from Solution

In certain embodiments of the invention, the polymer is recovered from solution. In such embodiments, after obtaining an aqueous process stream comprising the polymer that remains in solution, the polymer is recovered therefrom by a suitable recovery technique, examples of which are described herein.

Recovering the polymer from the aqueous process stream may be carried out by filtration, for example membrane filtration. As used herein, the term "membrane filtration" refers to any process of filtering a solution with a membrane which is suitable for concentrating and/or purifying a solution.

Preferably, the aqueous process stream comprises no or limited amounts of undissolved solids. The undissolved solids content of the aqueous process stream from which the polymer is recovered is low enough such that, upon further concentration, the solids will not increase the pressure of the filtration beyond the maximum which the membrane can withstand. Optimally, the aqueous process stream comprises no undissolved solids. The pH range of the aqueous process stream will vary depending on the nature of the stream selected for recovery of the polymer. The pH can range from between 2 and 10, more typically between 3 and 8.

The polymer is most advantageously recovered from the aqueous process stream by filtration that employs membranes with a cut-off of 500-100,000 Da for removing relatively large molecules. The polymer may be recovered from the aqueous process stream by using a membrane with pores that are small enough to retain the polymer, but large enough for water and other solutes to pass through. The molecular weight cut-off of the filtration membrane may be between 50 and 100,000 Da or between about 1,000 and 15,000 Da, between 1,500 and 12,000 Da or between 3,000 and 10,000 Da. As would be appreciated by those of skill in the art, the pore size selected can depend on various design parameters. Without being limiting, the molecular weight cut-off of the membrane may be selected so that it is half or one-third of the molecular weight of the polymer. By way of example, PEG-6000 may be recovered by using a membrane with a molecular weight cut-off of 3000 or 2000. Further, the selection of pore size may depend on the physical conformation of the species in solution.

The filtration membrane may be polymer-based, although inorganic materials, such as ceramic membranes are known as well. Examples of polymer-based membranes include cellulose and polyethersulfone. Filtration systems are commercially available from Sartorius AG, EMD Millipore® and Pall Corporation. The temperature of filtration can vary as required, although, as would be appreciated by those of skill in the art, the filtration rate may improve as the temperature is increased. Typical temperatures of filtration are 4° C. to 60° C. The flow through the membrane is generally carried out at elevated pressure to drive the filtration process. Similar to temperature, increases in pressure result in an increase in the filtration rate. A typical pressure range is from 2 to 5 bar.

The filtration may be a dead-end filtration in which the aqueous process stream is passed through the membrane and the solids are trapped in the filter with the permeate passing through. Alternatively, the filtration is a cross-flow filtration (also known as tangential flow filtration) in which the feed flow travels tangentially across the surface of the filter rather than passing through the filter as in dead-end filtration. An advantage of cross-flow filtration is that the filter cake is washed away during the filtration process, which can reduce blinding of the membrane and increase the length of time during which the filtration is operational. The filtration may also be a hybrid flow process which combines dead-end and cross-flow principles (e.g. a stirred cell design).

Subsequent to or during the filtration, the polymer is recovered from the membrane and a polymer stream is recycled for use in the process. In one embodiment, the filtration concentrates the polymer to within a range of between about 30 and 100 g/L or more typically between about 50 and 60 g/L. Alternatively, the filtration may concentrate the polymer from about 2 to 10 fold. The maximum polymer concentration may be limited by the pressure that builds up in the filtration equipment. The polymer stream may be added back to the hydrolysis of cellulose with cellulase. This allows the polymer to be reused in the process, which overcomes the high cost of adding the polymer to the hydrolysis. The degree of polymer concentration which is selected may be based on the desire to return only a small amount of water to the hydrolysis, which favors a high polymer concentration, offset by the decrease in filtration flux associated with highly concentrated streams.

It may be desirable to carry out dialysis of the aqueous process stream prior to or during a concentrating filtration for polymer recovery. In dialysis, small molecules pass through the membrane while the polymer is retained, but water is added to maintain the retentate concentration substantially constant. This has the advantage of maximizing the recovery of soluble sugars. Dialysis may be carried out by using a separate unit process from the filtration to recover the polymer. Alternately, dialysis may be carried out by using the polymer recovery unit, but with water addition prior to or during polymer recovery to maintain a low polymer concentration.

Lignin Uses

In certain embodiments of the invention, after recovery of the lignin solids, a process stream is obtained comprising recovered lignin solids resulting from the solids-liquid separation. The process stream comprising recovered lignin solids is used or provided for use in an application such as fuel production, energy generation, making a lignin-based product, or for any other suitable use.

The undissolved solids content of the process stream comprising recovered lignin solids resulting from the solids-liquid separation is typically between 20 wt % and 80 wt %, more typically between 30 wt % and 70 wt %. The lignin solids may comprise other undissolved components such as unconverted cellulose.

When used for energy generation, the process stream comprising recovered lignin solids may be used for heat or power production. The process stream comprising recovered lignin solids may be fed to an incinerator and the heat generated therein utilized to produce steam, process heat, building heat, electricity generation, or any combination of thereof. By the term "incinerator" it is meant any suitable device for combusting lignin. Depending on the water content, the lignin may be conveyed to the incinerator via a screw conveyor or other device for conveying solids.

The incinerator may include a boiler section in which water or other fluid is heated. The heat produced from the burning of these streams is transferred to boiler feed water to produce steam. The furnace may be a fluidized bed boiler, although other types of boilers may be used as required. The feed to the boiler may also include biogas produced during anaerobic digestion. Moreover, during the start-up stage of the process, a small amount of natural gas may be added to the furnace to heat the fuel to the ignition point. Depending on the emissions regulations, exhaust from the furnace may be passed to a scrubber or other series of operations to reduce pollutant levels before being discharged to the environment. As well, particulate matter may need to be removed from the exhaust. Ash from the system may be landfilled or sold as an additional co-product depending on its composition.

The steam may be used to drive turbines to create electricity for plant needs and/or can be sold to the power grid. Alternatively, or in addition to electricity generation, the steam can be used to supply process heat needs within the plant. If the steam is used within the plant, the pressure may be reduced prior to its re-use in the process. Examples of stages of the lignocellulosic conversion process to which steam can be supplied are pretreatment, fermentation, distillation, evaporation, fertilizer recovery and enzyme production. Furthermore, the steam can be utilized to provide building heating.

The recovered lignin solids may also be utilized for making a "lignin-based product", which is a product that contains lignin, or a lignin derivative, or a product that is produced by a conversion process that uses lignin as a starting material. By way of example, the lignin-based product may be an additive in a commercial application, a dispersant, a binder or an adhesive. An example of a conversion process is cracking lignin to produce aromatic compounds such as phenols.

DETAILED DESCRIPTION OF THE PREFERRED EMBODIMENTS

The process of the present invention will be described by reference to the figures. It should be understood, however, that the figures shown are merely exemplary of apparatus suitable for carrying out the present invention and other equivalent means may be utilized without departing from the spirit of the invention.

Figure 1B:
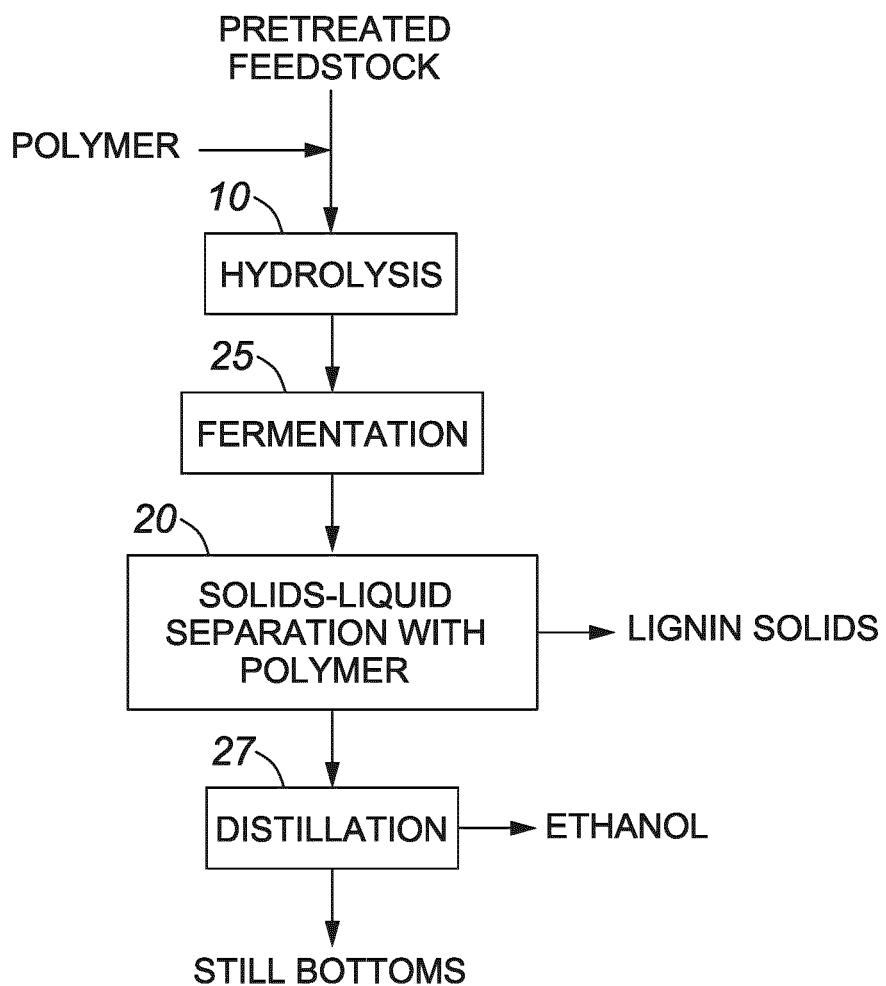
FIG. 1B shows a process in which a solids-liquid separation to recover lignin solids in the presence of polymer is performed on a fermentation beer resulting from fermentation with yeast to produce ethanol.
Figure 1C:
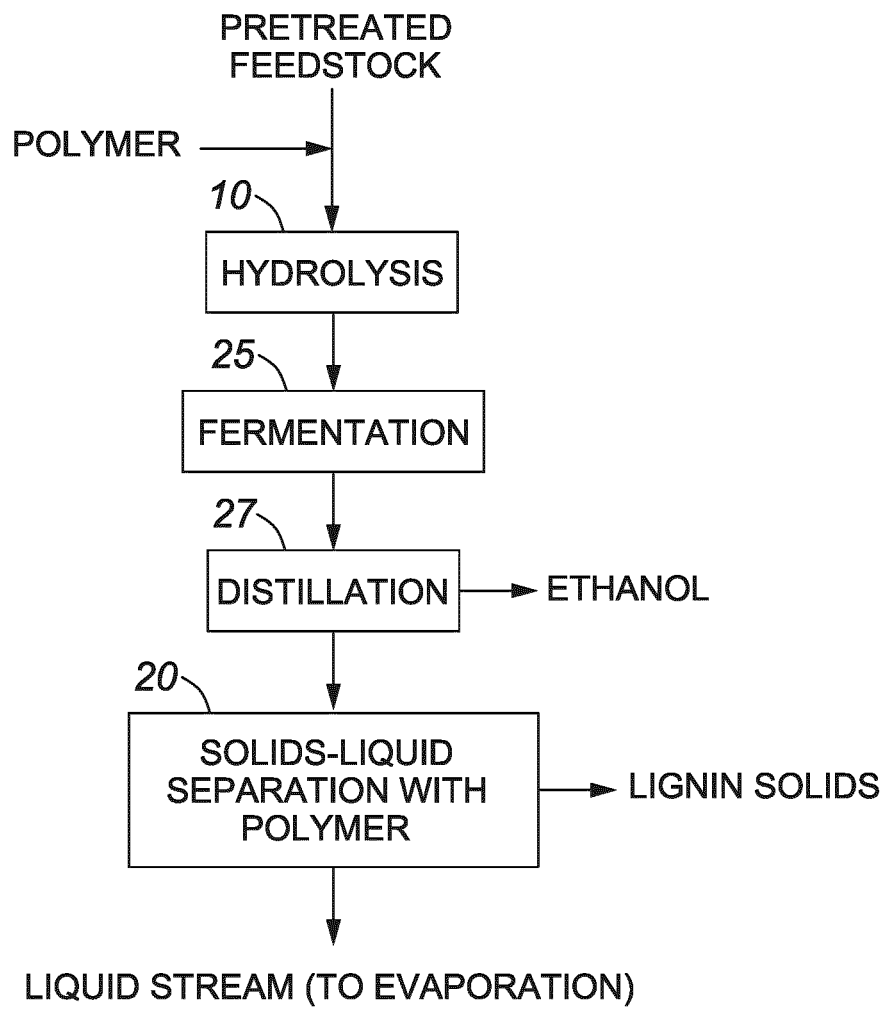
FIG. 1C shows a process in which a solids-liquid separation to recover lignin solids in the presence of polymer is performed on a still bottoms stream resulting from distillation to recover ethanol.

Referring now to FIGS. 1A-1C, there are shown examples of the process for recovering lignin solids conducted in accordance with embodiments of the invention. It should be appreciated that FIGS. 1A-1C are for illustrative purposes only and should not be construed to limit the current invention in any manner. Like reference numbers among the figures depict similar or identical streams or process steps.

As shown in FIG. 1A, there is shown a process in which a solids-liquid separation to recover lignin solids in the presence of polymer is performed on a hydrolyzed slurry resulting from cellulose hydrolysis with cellulase.

In this figure, polymer such as polyethylene glycol is added to an acid pretreated feedstock. The acid pretreated feedstock is prepared by hydrolyzing comminuted lignocellulosic feedstock with sulfuric acid to hydrolyze xylan to xylose, glucose, arabinose, mannose and galactose as disclosed in U.S. Pat. No. 4,461,648.

A polymer is added at a concentration of 2% to 20% weight of polymer on weight of undissolved pretreated solids. The acid pretreated feedstock is hydrolysed by cellulase enzymes comprising β-glucosidase in hydrolysis 10 to produce glucose.

The hydrolysed slurry resulting from hydrolysis 10 is then fed to solids-liquid separation 20 wherein the lignin solids are recovered. The solids-liquid separation 20 is carried out in the presence of the polymer. In this example, the solids-liquid separation 20 with polymer is conducted by a filter press that dewaters to a solids concentration of about 50-55 wt % to produce a filter cake. The solids-liquid separation 20 is improved in the presence of the polymer relative to its absence. The filtration performance is measured by determining the volume of water removed as a function of time, for a given filter area and cake solids loading. The improvement due to the addition of the polymer can be determined by comparing the filtration performance with and without polymer. The improvement can be depicted as a percent reduction in the filtration area or time, due to the presence of the polymer. In addition, the solids concentration of the lignin cake is higher.

The lignin filter cake from solids-liquid separation 20, comprising lignin solids and the polymer may be conveyed to a boiler. The polymer may optionally be removed. The heat energy from incinerating lignin in a boiler is used to generate steam for use in the process and/or to generate electricity in a turbine or for other uses as disclosed herein.

The hydrolyzed slurry from which lignin solids have been recovered is then fed to fermentation 25 where xylose, glucose or both sugars are converted to ethanol by a *Saccharomyces cerevisiae* yeast strain that is capable of converting both sugars to ethanol (see U.S. Pat. No. 5,789,210, incorporated herein by reference). The resultant ethanol-containing solution is fed to distillation 27 to concentrate the ethanol. Subsequently the ethanol-rich vapour is further concentrated by molecular sieves (not shown) to remove residual water. The still bottoms remaining after distillation may optionally be fed to an evaporation to increase the total solids to a desired value.

Referring now to FIG. 1B, there is shown a process in which a solids-liquid separation to recover lignin solids in the presence of polymer is performed on a fermentation beer resulting from fermentation with yeast to produce ethanol.

As shown in FIG. 1B, a polymer such as polyethylene glycol is added to an acid pretreated feedstock. The acid pretreated feedstock is prepared by hydrolyzing comminuted lignocellulosic feedstock with sulfuric acid to hydrolyze xylan to xylose, glucose, arabinose, mannose and galactose as disclosed in U.S. Pat. No. 4,461,648, which is incorporated herein by reference.

The polymer is added at a concentration of 2% to 20% weight of polymer on weight of undissolved pretreated solids. The acid pretreated feedstock is hydrolysed by cellulase enzymes comprising β-glucosidase in hydrolysis 10 to produce glucose.

The hydrolyzed slurry resulting from hydrolysis 10 is subsequently fed to a fermentation 25 without separating the lignin. In the fermentation 25, xylose and glucose are converted to ethanol by a *Saccharomyces cerevisiae* yeast strain that is capable of converting both sugars to ethanol (see U.S. Pat. No. 5,789,210, incorporated herein by reference). The resultant ethanol-containing solution or fermentation beer is fed to solids-liquid separation 20 wherein the lignin solids are removed. In this example, the solids-liquid separation with polymer 20 is conducted by a filter press that dewaters to a solids concentration of about 50-55 wt % to produce a filter cake. The solids-liquid separation 20 is improved in the presence of the polymer relative to its absence.

The lignin filter cake from solids-liquid separation 20, comprising lignin, the polymer and other undissolved solids derived from the fermentation beer, may be conveyed to a boiler. The polymer may be removed and recovered first. The heat energy from incinerating lignin in a boiler is used to generate steam for use in the process and/or to generate electricity in a turbine or for other uses as disclosed herein.

The fermentation beer from which lignin solids have been separated is fed to distillation 27 to concentrate the ethanol. Subsequently the ethanol-rich vapour is further concentrated by molecular sieves (not shown) to remove residual water. The still bottoms remaining after distillation may optionally be fed to an evaporation to increase the total solids to a desired value.

With reference to FIG. 1C, there is shown a process in which a solids-liquid separation to recover lignin solids in the presence of polymer is performed on a still bottoms stream remaining after distillation.

As shown in FIG. 1C, a polymer such as polyethylene glycol is added to an acid pretreated feedstock. The acid pretreated feedstock is prepared by hydrolyzing comminuted lignocellulosic feedstock with sulfuric acid to hydrolyse xylan to xylose, glucose, arabinose, mannose and galactose as disclosed in U.S. Pat. No. 4,461,648.

The polymer is added at a concentration of 2% to 20% weight of polymer on weight of undissolved pretreated solids. The acid pretreated feedstock is hydrolysed by cellulase enzymes comprising β-glucosidase in hydrolysis 10 to produce glucose.

The hydrolyzed slurry resulting from hydrolysis 10 is then fed to a fermentation 25 without separating the lignin solids. In the fermentation 25, xylose and glucose are converted to ethanol by a *Saccharomyces cerevisiae* yeast strain that is capable of converting both sugars to ethanol (see U.S. Pat. No. 5,789,210, incorporated herein by reference).

The resultant ethanol-containing solution is fed to distillation 27 to concentrate the ethanol. Subsequently the ethanol-rich vapor is further concentrated by molecular sieves (not shown) to remove residual water. The still bottoms remaining after distillation is fed to solids-liquid separation 20 wherein the lignin solids are recovered, along with other undissolved solids originating from fermentation and distillation in the presence of the polymer. In this example, the solids-liquid separation 20 is conducted by a filter press that dewaters to a solids concentration of about 50-55 wt % to produce a filter cake. The solids-liquid separation 20 is improved in the presence of the polymer relative to its absence. Moreover, the temperature of the still bottoms is 80-120° C., which further improves the filtration.

The lignin filter cake from solids-liquid separation 20, comprising lignin, the polymer and other undissolved solids derived from the still bottoms, may be conveyed to a boiler. The polymer may optionally be removed first. The heat energy from incinerating lignin in a boiler is used to generate steam for use in the process and/or to generate electricity in a turbine or for other uses as disclosed herein.

Figure 2A:
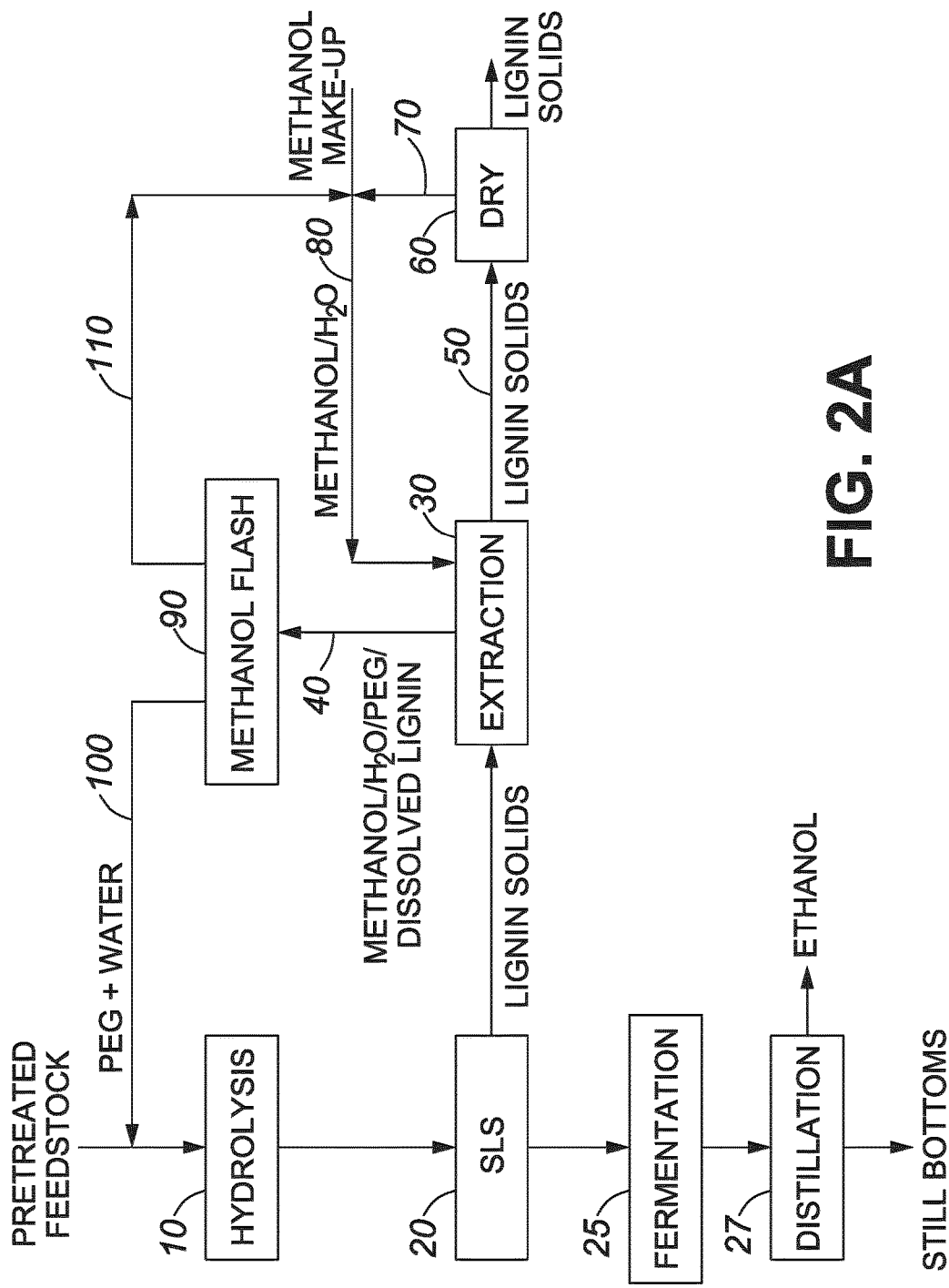
FIG. 2A shows a process in which a process stream comprising the polymer and lignin solids is recovered by a solids-liquid separation. The polymer is recovered from the lignin solids by a chemical extractant to recover the polymer. The recovered polymer is subsequently recycled for use in the process.
Figure 2B:
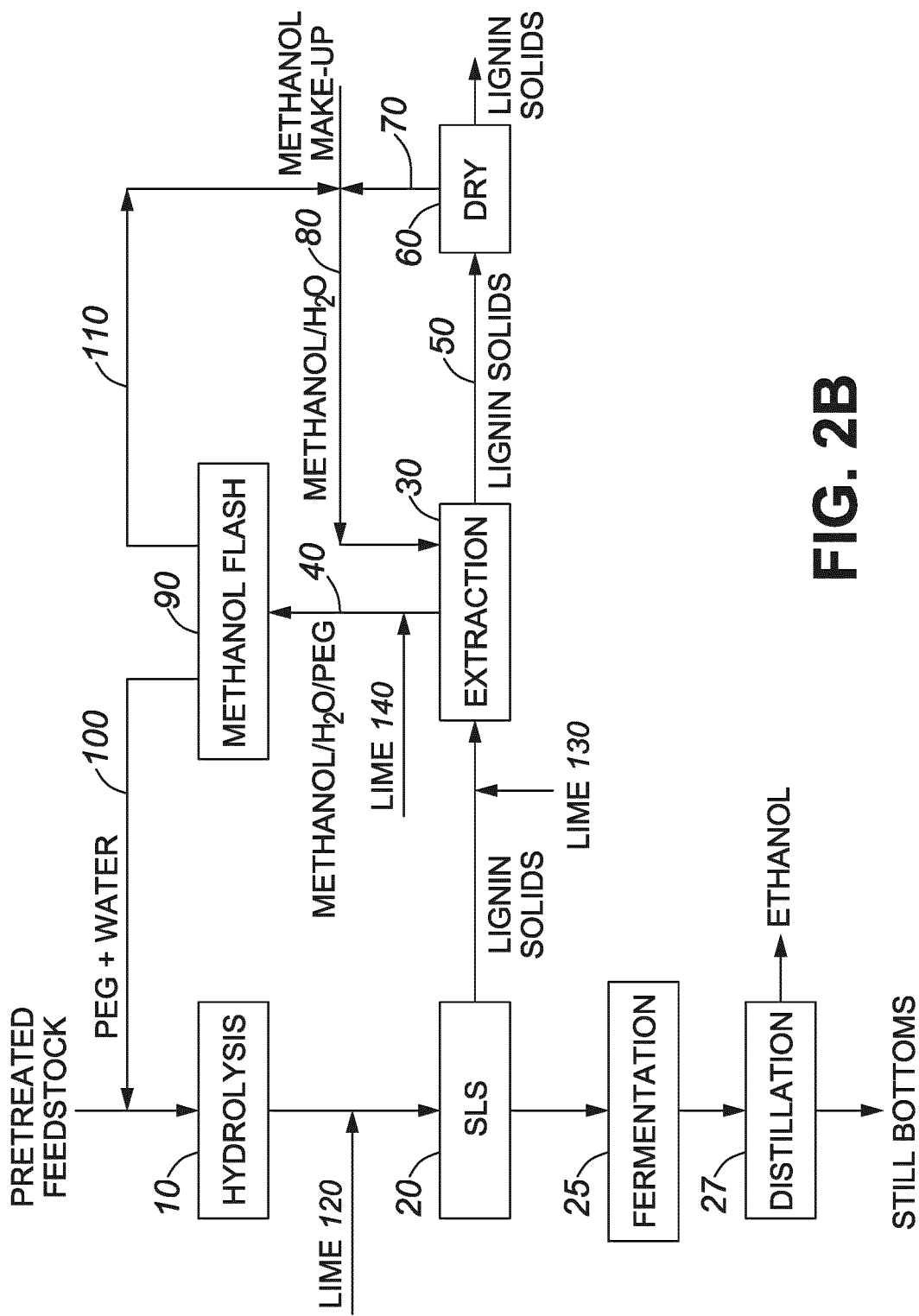
FIG. 2B depicts a process in which a process stream comprising the polymer and lignin solids is recovered by a solids-liquid separation. The polymer is recovered from the lignin solids by a chemical extractant to recover the polymer. The recovered polymer is subsequently recycled for use in the process. The process further comprises lime addition to a process stream comprising lignin solids and polymer to maintain the lignin insoluble and prevent dissolved lignin from being introduced back to hydrolysis upon recycle.
Figure 2C:
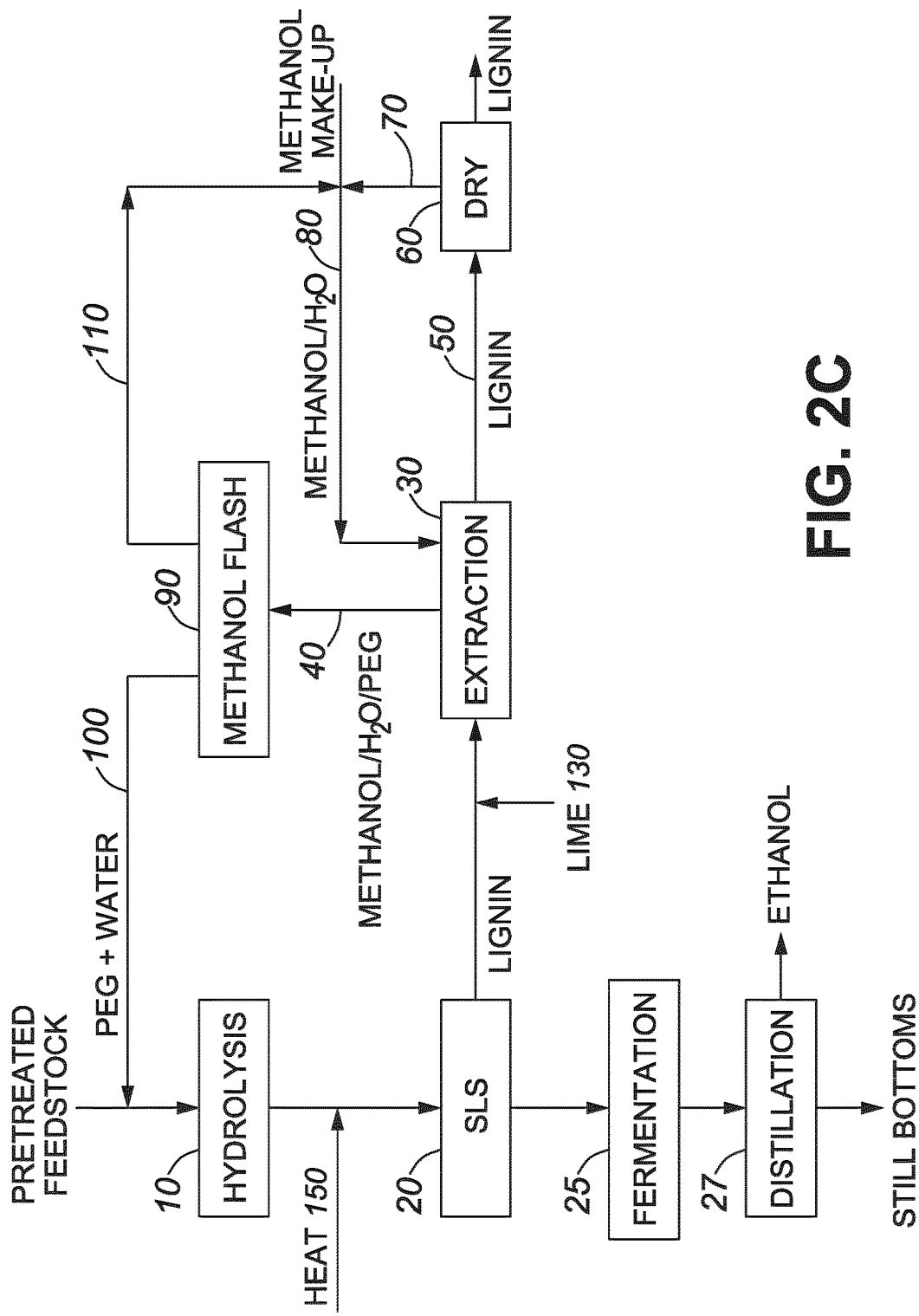
FIG. 2C depicts a process in which a process stream comprising the polymer and lignin solids is recovered by a solids-liquid separation. The polymer is recovered from the lignin solids by a chemical extractant to recover the polymer. The recovered polymer is subsequently recycled for use in the process. The process further comprises a heat treatment after hydrolysis and before the solids-liquid separation to bind or associate the polymer with the lignin solids.

Referring now to FIGS. 2A-2C there is shown examples of the process for recovering polymer and lignin solids conducted in accordance with embodiments of the invention.

In FIG. 2A, a polymer such as polyethylene glycol is added to an acid pretreated feedstock. The acid pretreated feedstock is prepared by hydrolyzing comminuted lignocellulosic feedstock with sulfuric acid to hydrolyze xylan to xylose, and produce some glucose, arabinose, mannose and galactose as disclosed U.S. Pat. No. 4,461,648.

The polymer is added at a concentration of 2% to 20% weight of polymer on weight of undissolved pretreated solids. The acid pretreated feedstock is adjusted to pH 4-6 with alkali and subsequently hydrolyzed by cellulase enzymes comprising β-glucosidase in hydrolysis 10 to produce a stream comprising glucose, sugars arising from pretreatment including xylose, arabinose, mannose and galactose, and lignin. The hydrolysis 10 is typically conducted at a temperature of 50-55° C.

The hydrolyzed slurry resulting from hydrolysis 10 is then fed to solids-liquid separation 20 wherein the lignin solids and polymer are separated, along with other unconverted undissolved solids. In this example, the solids-liquid separation 20 with polymer is conducted by a filter press that dewaters to a solids concentration of about 50-55 wt % to produce a filter cake. The liquid phase from the solids-liquid separation comprising glucose and the sugars hydrolyzed by pretreatment is then fed to fermentation 25 to produce ethanol and the ethanol is concentrated by distillation 27, as described further below in more detail.

The lignin filter cake from solids-liquid separation 20, comprising lignin solids, the polymer and other undissolved solids derived from the hydrolyzed slurry is then fed to an extraction 30. The extraction 30 is carried out by the addition of methanol to make a 50% solution of methanol in water 80, which recovers the polymer from the lignin solids. The result of the extraction 30 is an aqueous phase 40 which contains the extracted polymer, water, methanol and dissolved lignin and a lignin solids stream 50. The lignin solids stream 50 is fed to a drying step 60 where water and methanol is removed to produce a dried lignin solids stream. Methanol 70 recovered from drying step 60 is combined with a methanol/water stream 80. The methanol 70 and the methanol/water stream 80 feed the extraction 30. The dried lignin solids stream from drying 60 can be conveyed to a boiler. The heat energy from incinerating lignin solids in a boiler is used to generate steam for use in the process and/or to generate electricity in a turbine or for other uses as disclosed herein.

The aqueous phase containing polymer, water, dissolved lignin and the methanol 40 from the extraction 30 is fed to a methanol flash 90 where polymer, water and lignin are separated from the methanol. The methanol flash 90 produces a polymer-containing stream comprising polymer, water and lignin and a methanol stream 110. The methanol stream 110 is combined with the methanol/water stream 80 and a methanol make-up stream, which in turn is fed back to extraction 30. The methanol flash 90 causes the lignin in the polymer-containing stream to precipitate. This stream is sent to a solids-liquid separation (not shown) to separate the lignin solids from the polymer and water. The solids-liquid separation may be filtration or centrifugation. The polymer-containing stream 100 is re-circulated to hydrolysis 10.

As mentioned, after hydrolysis 10, the liquid phase from the solids-liquid separation 20 comprising glucose and the sugars produced by pretreatment, namely xylose, arabinose, mannose and galactose, is fed to the fermentation 25. During fermentation 25, xylose and glucose are converted to ethanol by a *Saccharomyces cerevisiae* yeast strain that is capable of converting both sugars to ethanol (see U.S. Pat. No. 5,789, 210, incorporated herein by reference). The resultant ethanol-containing solution (fermentation beer) is fed to the distillation 27 to concentrate the ethanol. Subsequently the ethanol-rich vapor is further concentrated by molecular sieves (not shown) to remove residual water. The still bottoms remaining after distillation may optionally be fed to an evaporation to increase the total solids to a desired value.

Referring now to FIG. 2B, there is shown a process that is identical to FIG. 2A, except lime is added to one or more process streams to maintain lignin solids in insoluble form. Lime is added in order to prevent or reduce any negative impact of dissolved lignin on the process. According to this embodiment, a process stream comprising soluble lignin and lignin solids is treated with calcium hydroxide to maintain the lignin in this stream insoluble. This can reduce process risk associated with recycling dissolved lignin along with the non-ionic polymer.

Lime may be added via lime stream 120 after hydrolysis 10 to the hydrolyzed slurry prior to the solids-liquid separation 20. According to this embodiment, lime is added to the hydrolyzed slurry in sufficient volume to adjust the pH of the hydrolyzed slurry to between 9 and 11. Lime addition at this point in the process maintains the lignin solids insoluble in the subsequent solids-liquid separation 20 and then in the subsequent extraction 30 with methanol. The polymer is then dissolved in the methanol in the absence of dissolved lignin. In this embodiment, the pH is adjusted to pH 4 to 5 prior to fermentation 25.

Lime may also be added via lime stream 130 to a lignin solids stream comprising lignin solids and polymer resulting from the solids-liquid separation 20. The lime is added in sufficient volume to the lignin solids stream to adjust the pH of the stream to between 9 and 11. Due to lime addition at this step, significant amounts of lignin solids do not dissolve during the subsequent extraction 30 with methanol.

In a further embodiment, lime is added via lime stream 140 to the solution comprising methanol, water, dissolved lignin and polymer resulting from extraction 30. In this embodiment, lime is added in sufficient amounts to adjust the pH of the solution comprising methanol, water, dissolved lignin and polymer to between 9 and 11. Lime addition at this location precipitates the lignin and forms a liquid phase that contains the dissolved polymer. The precipitated lignin is then separated from the soluble methanol/water/polymer stream (not shown).

FIG. 2C depicts a process that is identical to FIG. 2A, except a heat treatment, shown as heat addition 150 is conducted after hydrolysis 10 and before solids-liquid separation 20 to increase the binding or association of the polymer with lignin solids. In this example, the heat treatment resulting from heat addition 150 is conducted at 80° C. for 10 to 30 minutes.

As a result of the increased binding or association of the polymer to lignin solids, a larger proportion of the polymer binds to the lignin solids and less of the polymer is present in the aqueous solution. Since most, or all, of the polymer is bound to lignin solids, a greater portion of the polymer is carried through to extraction 30 along with lignin solids and recovered by desorption from lignin solids with methanol. Increasing the amount of polymer bound or associated with lignin solids can increase the amount of the polymer recovered from the lignin solids.

Although FIG. 2C depicts heat treatment by heat addition 150, the heat treatment can also be conducted as part of a distillation step, which is carried out at a temperature of between 90° C. and 125° C. In this embodiment, the solids-liquid separation 20 after hydrolysis 10 is eliminated so that the lignin solids and polymer is carried through to distillation and exposed to heat treatment by distillation. The solids-liquid separation is then conducted on the still bottoms stream to obtain a solids stream comprising the lignin solids and polymer. The solids stream derived from the still bottoms is subsequently fed to the extraction 30 to recover the polymer for recycle.

In addition to heat treatment resulting from heat addition 150, the process comprises lime addition via lime stream 130 to maintain the lignin insoluble, thereby reducing any negative impact of recycling dissolved lignin as discussed above with reference to FIG. 2B.

Figure 3:
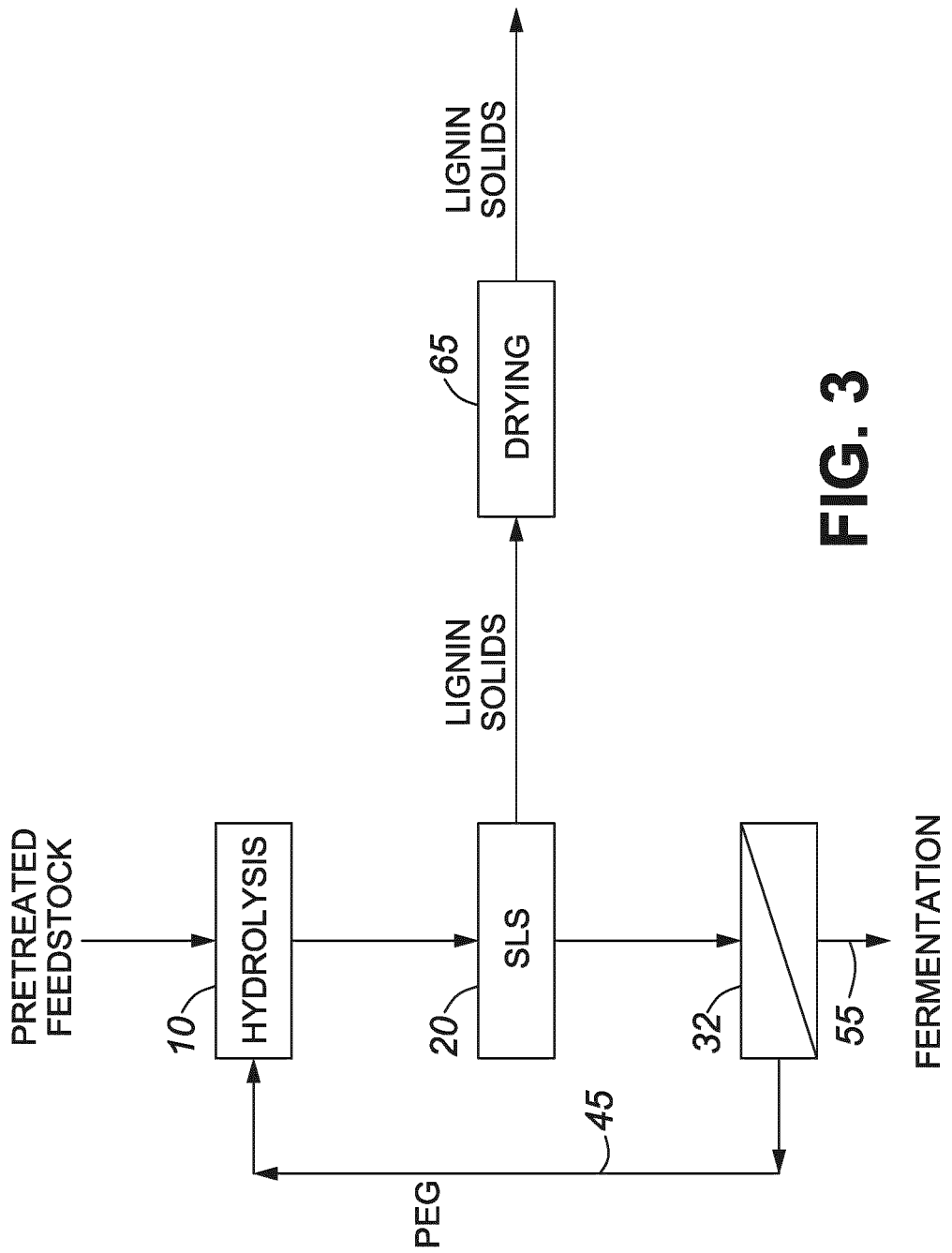
FIG. 3 depicts a process in which a pretreated lignocellulosic feedstock is hydrolyzed with cellulase enzymes in the presence of a polymer. After the hydrolysis, an aqueous process stream comprising the polymer is recovered by a solids-liquid separation. The polymer is recovered from the aqueous process stream by ultrafiltration. The recovered polymer is subsequently recycled for use in the process.

FIG. 3 depicts a process in which polymer is recovered from aqueous solution by the use of ultrafiltration. As shown in FIG. 3, a polymer such as polyethylene glycol is added to an acid pretreated feedstock. In this example, the polyethylene glycol has a molecular weight of 6000 (PEG-6000). The acid pretreated feedstock is prepared by hydrolyzing comminuted lignocellulosic feedstock with sulfuric acid to hydrolyze xylan to xylose and produce some glucose, arabinose, mannose and galactose as disclosed in U.S. Pat. No. 4,461,648.

The PEG-6000 is added at a concentration of 2% to 20% weight of polymer on weight of undissolved pretreated solids. The acid pretreated feedstock is adjusted to pH 4-6 with alkali and subsequently hydrolysed by cellulase enzymes comprising β-glucosidase in hydrolysis 10 to produce a stream comprising glucose, sugars arising from pretreatment including xylose, arabinose, mannose and galactose, and lignin. The hydrolysis is typically conducted at a temperature of 50-55° C.

The hydrolyzed slurry resulting from hydrolysis 10 is then fed to solids-liquid separation 20 to produce a stream comprising lignin solids and PEG-6000 bound or associated with the lignin solids and an aqueous process stream comprising polymer that remains in solution. In this example, the solids-liquid separation 20 with PEG-6000 is conducted by a filter press.

The aqueous process stream from the solids-liquid separation 20 comprises a portion of the PEG-6000 that does not bind to the lignin solids. The PEG-6000 remaining in the aqueous process stream after solid-liquid separation is recovered by ultrafiltration 32. The ultrafiltration membrane has pores that are small enough to retain the PEG-6000, but large enough for water, sugars and other soluble components to permeate. In this example, the molecular weight cutoff is 5000 so as to retain the PEG having a molecular weight of 6000. The PEG-6000 is subsequently recovered from the ultrafiltration membrane and recycled to hydrolysis 10 via polymer stream 45.

The permeate stream 55 from the ultrafiltration membrane comprises water, sugars and other soluble components. In this example, the sugars comprise glucose and the sugars produced by pretreatment, namely xylose, arabinose, mannose and galactose. The permeate stream 55 is fed to fermentation where the sugars are fermented to ethanol. During fermentation, xylose and glucose are converted to ethanol by a *Saccharomyces cerevisiae* yeast strain that is capable of converting both sugars to ethanol (see U.S. Pat. No. 5,789,210, incorporated herein by reference). The resultant ethanol-containing solution (fermentation beer) is fed to a distillation to concentrate the ethanol (not shown). Subsequently, the ethanol-rich vapour is further concentrated by molecular sieves (not shown) to remove residual water.

The lignin solids resulting from the solids-liquid separation 20 are fed to drying step 65 where water is removed to produce a dried lignin stream. The dried lignin stream can be conveyed to a boiler. The heat energy from incinerating lignin in a boiler is used to generate steam for use in the process and/or to generate electricity in a turbine or for other uses as disclosed herein.

EXAMPLES

Example 1: Measurement of Polymer Bound to Lignin Solids and Remaining in Solution Corn stover was pretreated with high pressure steam and dilute sulfuric acid in a steam explosion process by the procedures of U.S. Pat. No. 4,461,648. The pretreated feedstock was washed with water and filtered. The resulting washed, pretreated solids comprise 58.8 wt % cellulose and 27.9 wt % undissolved solids. The washed, pretreated solids were hydrolyzed with an enzyme mixture comprising cellulase enzymes and β-glucosidase in a 250 mL flask containing 8 grams of undissolved solids, 56 mg polyethylene glycol of molecular weight 6000 (PEG-6000, purchased from Sigma Chemical Company) per gram of undissolved solids, and the balance was adjusted to 100 grams with water. The pH was adjusted to 5.2+/−0.1 with 2 M NaOH. The flask was incubated at 50° C. with shaking for 2 hours and subsequently 8 mg of Novozymes Cellic® CTec2 cellulase enzyme per gram cellulose was added to the flask. The pH was periodically checked and adjusted to pH 5.2 as needed.

After 96 h, the cellulose conversion was 94% as determined by measuring the glucose concentration in the liquid and relating it to the initial cellulose concentration. The hydrolysis was terminated at this point by filtration. The undissolved solids concentration was 3.57 wt %, which corresponds to the concentration of lignin solids, and the corresponding mass was 3.57 grams. The concentration of PEG-6000 in the liquid was 3.3 mg/mL as measured by HPLC (Varian HPLC with a size exclusion column and refractive index detector). As the liquid volume was 92 mL, the mass of PEG-6000 in solution was (92 mL) (3.3 mg/mL)=303.6 mg. The mass of PEG-6000 added initially was (56 mg/g)(8 g)=448 mg. The amount of PEG-6000 bound to the lignin solids was therefore 448−303.6=145.4 mg. This corresponds to 145.4 mg/3.57 g lignin solids=40.7 mg PEG-6000 per gram lignin solids. In addition, 303.6 mg of the 448 mg of PEG-6000 originally added remains in solution, which corresponds to 67.6% of the amount of originally added PEG.

Example 2: Improved Filtration of Lignin Solids with Polymer

Corn stover was pretreated with high pressure steam and dilute sulfuric acid in a steam explosion process by the procedures of U.S. Pat. No. 4,461,648. The pretreated feedstock was washed with water and filtered. The resulting washed, pretreated solids comprise 58.8% cellulose and 27.9% undissolved solids. The washed, pretreated solids were hydrolyzed with an enzyme mixture comprising cellulase enzymes and β-glucosidase in two 250 mL flasks, each containing 8 grams of undissolved solids. One flask contained 56 mg polyethylene glycol of molecular weight 6000 (PEG-6000) per gram of undissolved solids, while the other contained no added PEG-6000. The content of each flask was brought up to 100 grams by the addition of water and the pH was adjusted to 5.2+/−0.1 with 2 M NaOH. Each flask was incubated at 50° C. with shaking for 2 hours and then 8 mg of Novozymes Cellic® CTec2 cellulase enzyme per gram cellulose was added. The pH was monitored and adjusted to pH 5.2 as needed.

After 96 h, the hydrolysis was terminated. Aliquots of the flasks of 5 mL were filtered over a 1.7-inch diameter Buchner funnel with Whatman No. 5 cellulose filter paper without prior cooling of the aliquot. The time to complete the filtration and the rate of filtration are shown in the table below. The presence of the polymer increased the rate of filtration 5-fold.

TABLE 1

| | Filtration time and rate | |
|---|---|---|
| Sample | Time to filter (sec) | Filtration rate (mL/sec) |
| With PEG added | 24 | 0.20 |
| Without PEG added | 125 | 0.0384 |

Example 3: Improved Filtration of Lignin Solids with Polymer at 80° C.

This example uses the procedures as set out in Example 2 to carry out the enzymatic hydrolysis and filtration, except at the termination of each hydrolysis the flasks were heated from 50° C. to 80° C. The filtration of the lignin solids was subsequently carried out as described in Example 2, without any cooling of the slurry. The time to complete the filtration is shown in Table 2. The presence of the polymer increased the rate of filtration by 5-fold.

TABLE 2

| | filtration time and rate at 80° C. | |
|---|---|---|
| Sample | Time to filter (sec) | Filtration rate (mL/sec) |
| With PEG added | 6 | 0.80 |
| Without PEG added | 32 | 0.15 |

Example 4: Improved Dewatering of Lignin Solids with Polymer

This example uses the procedures as set out in Examples 2 and 3 to carry out the enzymatic hydrolysis and filtration except included an additional step of determining the solids content of the filter cake by heating overnight at 105° C. in a drying oven. The solids content of each filter cake is shown in Table 3. The presence of the polymer increased the cake solids by 1.25-fold at 50° C. and 1.55-fold at 80° C. The corresponding decrease in water content of each filter cake allows for greater ease in drying of the lignin solids.

TABLE 3

Solids and water content of filter cakes

| Sample | Cake solids (%) | | Water content (%) | |
|---|---|---|---|---|
| | 50° C. | 80° C. | 50° C. | 80° C. |
| With PEG added | 47.5% | 63.5% | 52.5% | 36.5% |
| Without PEG added | 38.3% | 41.0% | 61.7% | 59.0% |

Example 5: Improved Recovery of Sugar from Lignin Solids with Polymer

This example uses the procedures as set out in Examples 2 to 4 to carry out the enzymatic hydrolysis and filtration. In addition, the percentage of the water removed during the filtration was determined. From these values the potential sugar loss (in percent) to the filter cake could be determined as well. This is shown in Table 4 below. The presence of the polymer decreased the potential sugar losses by 51% at 50° C. and 67% at 80° C.

TABLE 4

Water removal during filtration

| Sample | Water removal (%) | | Potential sugar losses (%) | |
|---|---|---|---|---|
| | 50° C. | 80° C. | 50° C. | 80° C. |
| With PEG added | 95.7% | 97.8% | 4.3% | 2.2% |
| Without PEG added | 91.2% | 93.2% | 8.8% | 6.8% |

Example 6: Heat Treatment to Increase Polymer Binding to Lignin Solids

Corn stover was pretreated with high pressure steam and dilute sulfuric acid in a steam explosion process by the procedures of U.S. Pat. No. 4,461,648. The pretreated material was washed with water and filtered. The resulting washed, pretreated solids comprise 58.8% cellulose and 27.9% UDS. The washed, pretreated solids, PEG-6000 and water were added to a 250 mL flask for enzymatic hydrolysis. The flask contained 8 grams of undissolved pretreated solids, 56 mg PEG-6000 per gram of undissolved, pretreated solids, and the final flask content by weight was adjusted to 100 grams with water. The pH was adjusted to 5.2+/−0.1 with 2 M NaOH. The flask was incubated at 50° C., shaking, for 2 hours and then 8 mg of Novozymes Cellic® CTec2 cellulase enzyme per gram cellulose was added to the flask. The pH was periodically checked and adjusted to pH 5.2 as needed.

After 97 h, the cellulose conversion was 94% as determined by measuring the glucose concentration in the liquid and relating it to the initial cellulose concentration. A sample was taken and filtered over a Buchner funnel with Whatman No. 5 filter paper. The concentration of PEG-6000 in the filtrate was 2.17 mg/mL (measured by Varian HPLC with size exclusion column and refractive index detector). As the liquid volume was 92 mL, the mass of PEG-6000 in solution was (92 mL)(2.17 mg/mL)=199.4 mg. The mass of PEG-6000 added initially was (56 mg/g)(8 g)=448 mg. The amount of PEG-6000 bound to the lignin solids was therefore 448−199.4=248.6 mg. This corresponds to 248.6 mg/448 mg added, which in turn equates to 55.5% of the PEG-6000 added.

To measure the effect of heat treatment on the proportion of PEG bound to lignin solids, a 5 mL aliquot was withdrawn from the hydrolysis flask and placed in a 50 mL Falcon conical sample tube. The tube was placed in an 80° C. incubator shaker for 30 minutes. The tube contents were then immediately filtered by using a Buchner funnel with Whatman No. 5 filter paper. The measured concentration of PEG-6000 in solution was 0.38 mg/mL. This corresponds to 7.8% of the polymer in solution, and therefore 92.2% bound to the lignin solids. The 80° C. heat treatment had therefore increased the proportion of PEG bound to the lignin solids from 55.5% to 92.2%.

Example 7: Extraction of Polymer from Lignin Solids by Using Alcohols

Corn stover was pretreated with high pressure steam and dilute sulfuric acid in a steam explosion process by the procedures of U.S. Pat. No. 4,461,648. The pretreated material was washed with water and filtered. The resulting washed, pretreated solids comprise of 58.8% cellulose and 27.9% UDS. The washed, pretreated solids, PEG-6000 and water were added to a 250 mL flask for enzymatic hydrolysis. The flask contained 8 grams of undissolved solids, 56 mg of PEG-6000 per gram of undissolved solids, and the flask content was adjusted to 100 grams with water. The pH was adjusted to 5.2+/−0.1 with 2 M NaOH. The flask was incubated at 50° C., shaking, for 2 hours and then 8 mg of Novozymes Cellic® CTec2 cellulase enzyme per gram cellulose was added to the flask. The pH was periodically checked and adjusted to pH 5.2 as needed.

After 97 h, the cellulose conversion was 94% as determined by measuring the glucose concentration in the liquid and relating it to the initial cellulose concentration.

Several 5 mL aliquots were taken from the hydrolysis flask and placed in a 50 mL Falcon conical sample tube with 5 mL of extractant solutions, including a water control brought through the procedure. The extraction was carried out at ambient temperature for 5 minutes, at which point the tube contents were centrifuged for 2 minutes at 4000 RPM. The concentration of PEG-6000 in solution was measured as described in Example 6, with the exception of the 25% n-butanol extractant, in which case only the aqueous phase was analyzed. The results are shown in Table 5.

TABLE 5

Extraction of PEG-6000 with alcohols

| Extractant | PEG-6000 in solution (mg/mL) | PEG-6000 in solution (percentage of total added) |
|---|---|---|
| None (Hydrolysis final sample) | 2.30 | 47% |
| Water | 1.15 | 47% |
| 10% ethanol | 1.46 | 60% |
| 40% methanol | 1.73 | 71% |
| 40% ethanol | 2.07 | 85% |
| 40% isopropanol | 2.10 | 86% |
| 25% n-butanol | 2.24 | 92% (aqueous phase) |

The present invention has been described with regard to one or more embodiments and examples. However, it will be apparent to persons skilled in the art that a number of variations and modifications can be made without departing from the scope of the invention as defined in the claims.

The invention claimed is:

1. A process for hydrolyzing a pretreated lignocellulosic feedstock and recovering lignin solids comprising:
   (i) hydrolyzing the pretreated lignocellulosic feedstock with an enzyme mixture comprising at least cellulase enzymes to produce a hydrolyzed slurry comprising glucose and lignin solids, said hydrolyzing being conducted in the presence of a polymer that binds or associates with the lignin solids;
   (ii) conducting a solids-liquid separation to recover lignin solids from a process stream comprising the lignin solids and the polymer;
   (iii) obtaining a process stream comprising recovered lignin solids resulting from the solids-liquid separation of step (ii), and
   (iv) recovering at least a portion of the polymer from the recovered lignin solids of step (iii) comprising adding a chemical extractant selected from alcohol or alkali for extracting the at least a portion of the polymer, and further recovering the chemical extractant and recycling both the recovered polymer and the chemical extractant in the process.

2. The process of claim 1, wherein the polymer that binds or associates with the lignin solids is a non-ionic polymer.

3. The process of claim 2, wherein the non-ionic polymer is a water-soluble polymer.

4. The process of claim 3, wherein the water-soluble polymer is a polyether or a surfactant comprising a polyether.

5. The process of claim 4, wherein the polyether is paraformaldehyde, polyethylene glycol, polypropylene glycol, polytetramethylene glycol or a substituted aliphatic polyether.

6. The process of claim 1, wherein the polymer is added at a concentration of 2% to 20% by weight based on the weight of undissolved pretreated solids.

7. The process of claim 1, wherein in the step of conducting a solids-liquid separation to recover the lignin solids from a process stream comprising the lignin solids and the polymer, at least 50 wt % of the process stream is fed to the solids-liquid separation.

8. The process of claim 1, wherein the solids-liquid separation is filtration.

9. The process of claim 1, wherein the process stream of step (ii) is a fermentation broth or a still bottoms stream.

10. The process of claim 1, wherein the lignin solids in the process stream of step (ii) comprises dissolved lignin.

11. The process of claim 1, wherein the chemical extractant in step (iv) is an alcohol.

12. The process of claim 11, wherein the process stream comprising the lignin solids and the polymer is heat treated, treated with lime, or a combination thereof, prior to recovery of the polymer.

13. The process of claim 1, further comprising recovering at least another portion of the polymer from solution of an aqueous process stream, said aqueous process stream obtained from the solids-liquid separation in step (ii).

14. The process of claim 1, wherein conducting the solids-liquid separation comprises filtering the process stream when the process stream is at a temperature between 55° C. and 200° C.

15. The process of claim 1, wherein the polymer comprises polyethylene glycol.

16. The process of claim 11, wherein the alcohol is ethanol.

17. The process of claim 11, wherein the alcohol is methanol.

18. The process of claim 14, wherein the temperature is at least 80° C. and less than 200° C.

19. A process for producing an alcohol from a lignocellulosic feedstock comprising:
   hydrolyzing a pretreated lignocellulosic feedstock with an enzyme mixture comprising at least cellulase enzymes to produce a hydrolyzed slurry comprising glucose and lignin solids, said hydrolyzing being conducted in the presence of a polymer that binds or associates with the lignin solids;
   (ii) fermenting the glucose to produce a fermentation beer comprising the alcohol and then concentrating the alcohol;
   (iii) conducting a solids-liquid separation to recover the lignin solids from a process stream comprising the lignin solids and the polymer;
   (iv) obtaining a process stream comprising recovered lignin solids resulting from the solids-liquid separation of step (iii), and
   (v) recovering at least a portion of the polymer from the recovered lignin solids of step (iii) comprising adding a chemical extractant selected from an alcohol or alkali for extracting the at least a portion of the polymer, further recovering the chemical extractant and recycling both the recovered polymer and the chemical extractant in the process.

20. The process of claim 19, wherein the process stream comprising the lignin solids and the polymer in step (iii) is the hydrolyzed slurry, the fermentation beer, a still bottoms stream remaining from concentrating the alcohol, or a combination thereof.

* * * * *